US010595742B2

(12) United States Patent
Li et al.

(10) Patent No.: US 10,595,742 B2
(45) Date of Patent: Mar. 24, 2020

(54) SYSTEM AND METHOD FOR CLASSIFICATION OF BODY ACTIVITIES WITH ON-BODY ANTENNA REFLECTION COEFFICIENT

(71) Applicant: BAYLOR UNIVERSITY, Waco, TX (US)

(72) Inventors: Yang Li, Waco, TX (US); Youngwook Kim, Fresno, CA (US)

(73) Assignee: Baylor University, Waco, TX (US)

( * ) Notice: Subject to any disclaimer, the term of this patent is extended or adjusted under 35 U.S.C. 154(b) by 107 days.

(21) Appl. No.: 15/616,031

(22) Filed: Jun. 7, 2017

(65) Prior Publication Data

US 2017/0360323 A1 Dec. 21, 2017

Related U.S. Application Data

(60) Provisional application No. 62/468,148, filed on Mar. 7, 2017, provisional application No. 62/352,808, filed on Jun. 21, 2016.

(51) Int. Cl.
*A61B 5/05* (2006.01)
*G06K 9/00* (2006.01)
(Continued)

(52) U.S. Cl.
CPC .............. *A61B 5/05* (2013.01); *A61B 5/7246* (2013.01); *A61B 5/7267* (2013.01); *G01N 22/00* (2013.01);
(Continued)

(58) Field of Classification Search
CPC ....... A61B 5/05; A61B 5/7246; A61B 5/7267; A61B 2560/0223; G01N 22/00; G06K 9/00342
(Continued)

(56) References Cited

U.S. PATENT DOCUMENTS

2012/0106298 A1* 5/2012 Liu ..................... G06K 9/00335
367/87
2014/0266860 A1* 9/2014 Blumrosen ............... A61B 8/08
342/106

OTHER PUBLICATIONS

Lorincz et al., "Mercury: A Wearable Sensor Network Platform for High-Fidelity Motion Analysis", SenSys 09, p. 1-14, 2009.*
(Continued)

*Primary Examiner* — Daniel L Cerioni
(74) *Attorney, Agent, or Firm* — Jackson Walker, LLP

(57) ABSTRACT

A system and method for classifying body activities through an on-body antenna measuring changes in reflected power and the resulting reflection coefficients, in contrast to two antenna systems that measure transmission power therebetween. A single on-body antenna can be attached or held in close proximity to the body. The antenna can be calibrated based on changes in the reflection coefficients for various calibration activities for the location at which the antenna is placed on the body. Magnitude changes and patterns of the reflection coefficients at a given frequency for a given activity can be compared with calibrated data to correlate a given activity. Further accuracy can be gained by comparing both magnitude and phase changes and patterns at a given frequency with calibrated data for a given activity. The antenna can use power losses from a transmitted signal to measure the changes in the reflected power to minimize power requirements.

15 Claims, 24 Drawing Sheets

(51) Int. Cl.
*A61B 5/00* (2006.01)
*G01N 22/00* (2006.01)

(52) U.S. Cl.
CPC .. *G06K 9/00342* (2013.01); *A61B 2560/0223* (2013.01)

(58) Field of Classification Search
USPC .......................................................... 600/595
See application file for complete search history.

(56) References Cited

OTHER PUBLICATIONS

Hughes et al., "Switchback: An On-Body RF-based Gesture Input Device", ACM, ISWC 14, pp. 63-66, 2014.*

Guraliuc et al., "Limb Movements Classification using Wearable Wireless Transceivers", IEEE, IT Biomedicine, vol. 15, No. 3, pp. 474-480, 2011.*

Dynamic Time Warping [retrieved from Internet on Jun. 6, 2016 using <URL: https://en.wikipedia.org/wiki/Dynamic_time_warping], 6 pages.

Deep Learning [retrieved from Internet on Jun. 6, 2016 using <URL: https://en.wikipedia.org/wiki/Deep_learning], 30 pages.

Youngwook Kim and Yang Li. Human Activity Classification With Transmission and Reflection Coefficients of On-Body Antennas Through Deep Convolutional Neural Networks. IEEE Transactions on Antennas and Propagation, vol. 65, 2017, at pp. 2764-2768.

Yang Li and Youngwook Kim, Classification of Human Activities Using Variation in Impedance of Single On-Body Antenna. IEEE Antennas Wireless Propagation Letters, vol. 16, 2016, at pp. 541-544.

Anda R. Guraliuc, Paolo Barsocchi, Francesco Potortl, and Paolo Nepa. Limb Movements Classification Using Wearable Wireless Transceivers. IEEE Transactions on Information Technology in Biomedicine, vol. 15, 2011, at pp. 474-480.

Erika Pittella. Breath Activity Monitoring With Wearable UWB Radars: Measurement and Analysis of the Pulses Reflected by the Human Body. IEEE Transactions on Biomedical Engineering, vol. 63, 2016, at pp. 1447-1454.

John Buckley, Kevin G. McCarthy, Brendan O'Flynn, Cian O' Mathuna. The Detuning Effects of a Wrist-Worn Antenna and Design of a Custom Antenna Measurement System. Wireless Technology Conference (EuWIT), EU, 2010 at pp. 1738-1741.

International Search Report and Written Opinion dated Sep. 11, 2017 for International Application No. PCT/US2017/038108 (13 pages).

* cited by examiner

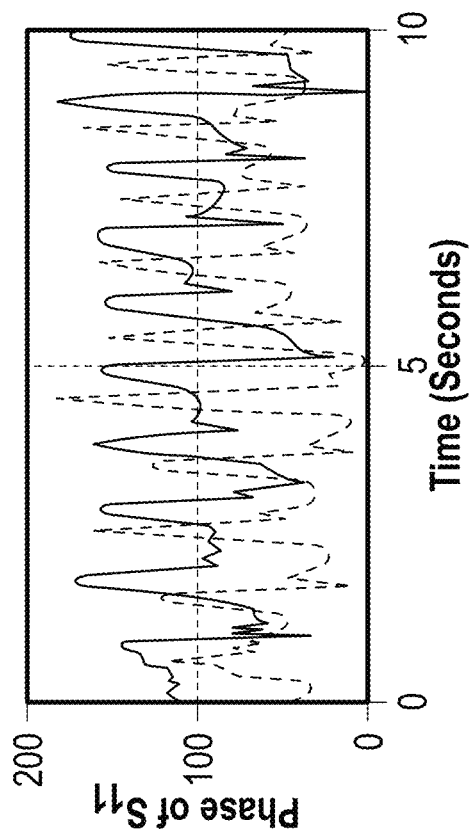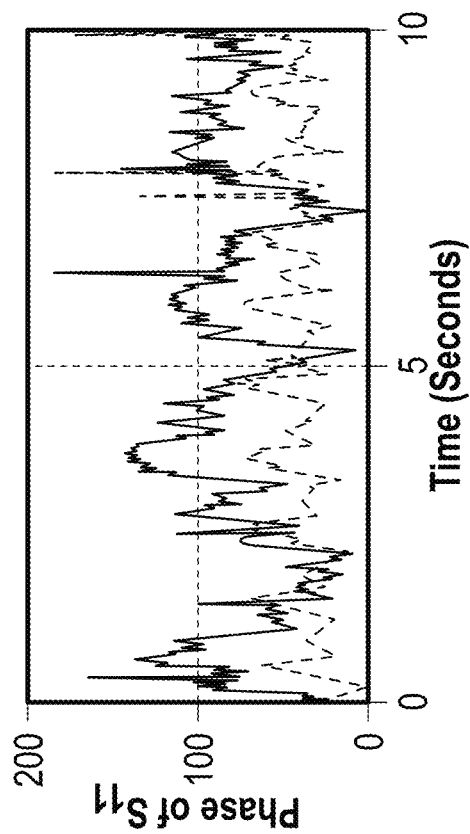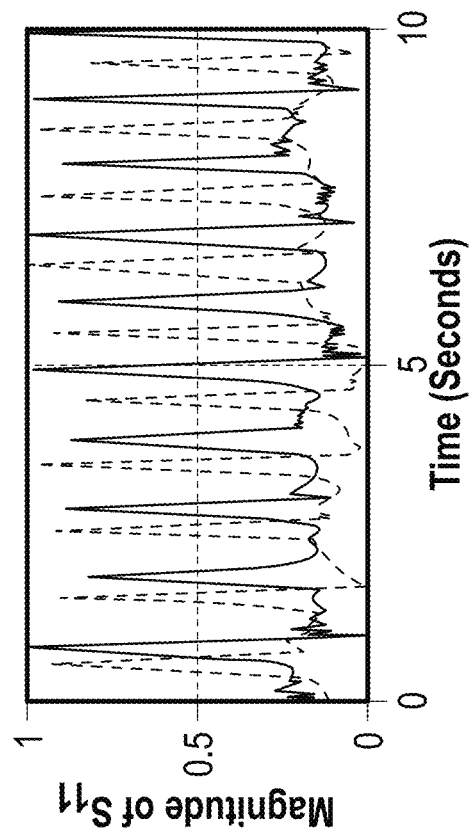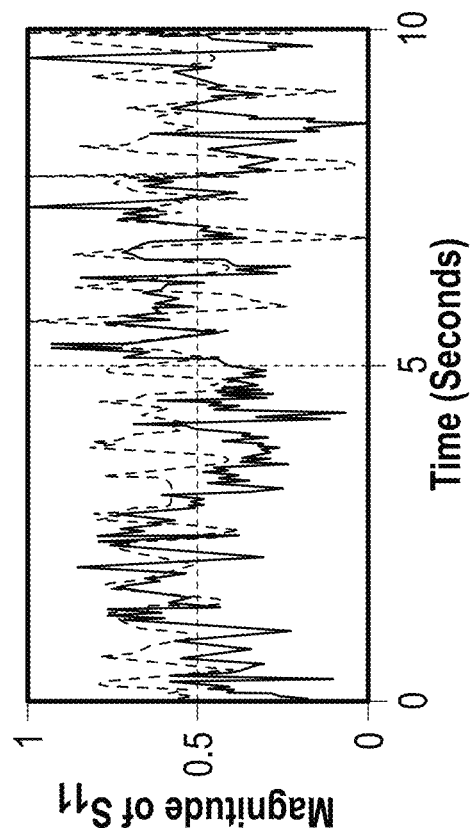
FIG. 12A
FIG. 12B
FIG. 13A
FIG. 13B

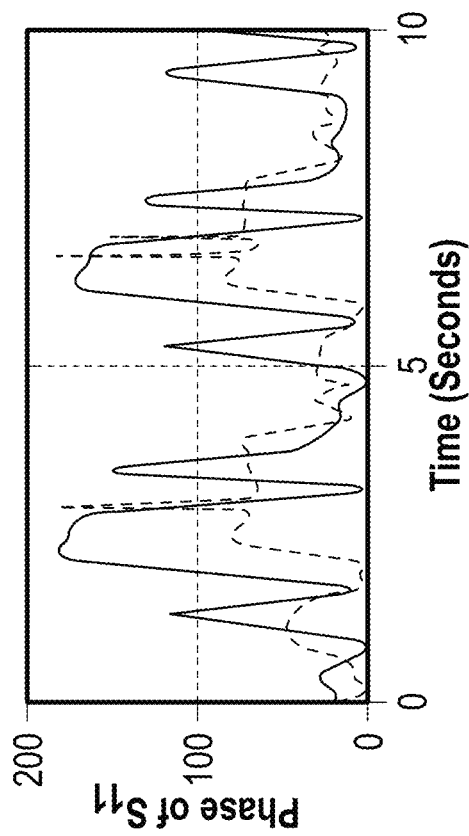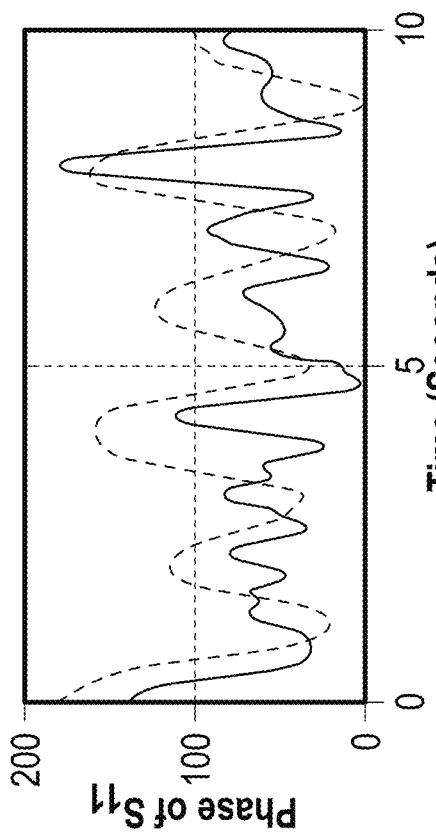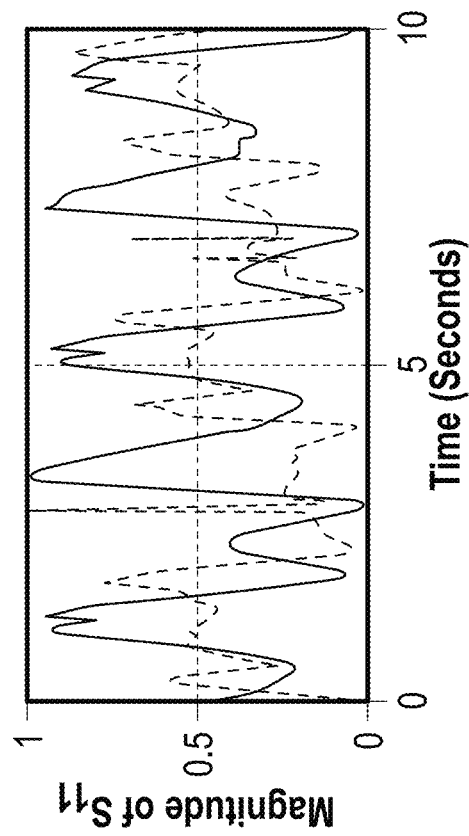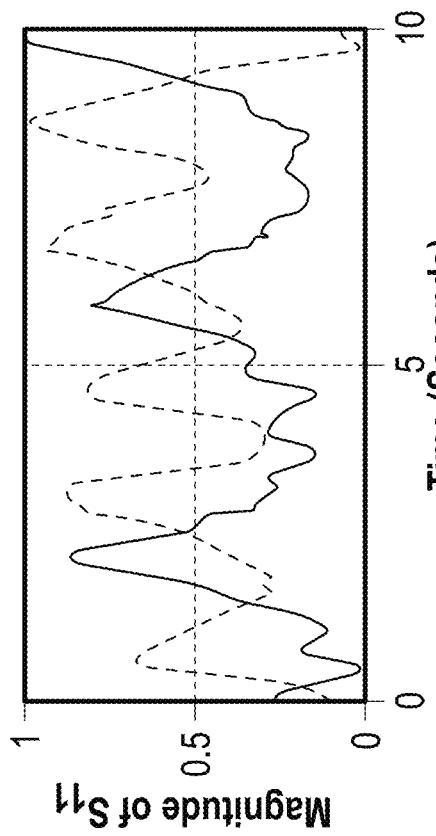
FIG. 12E
FIG. 12F
FIG. 13E
FIG. 13F

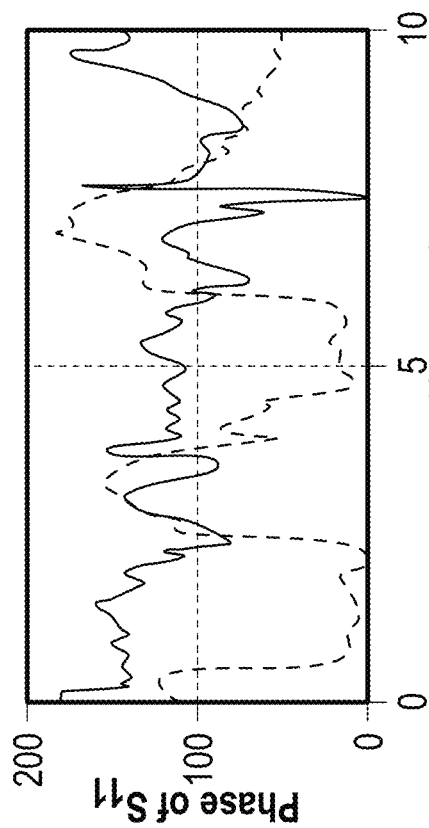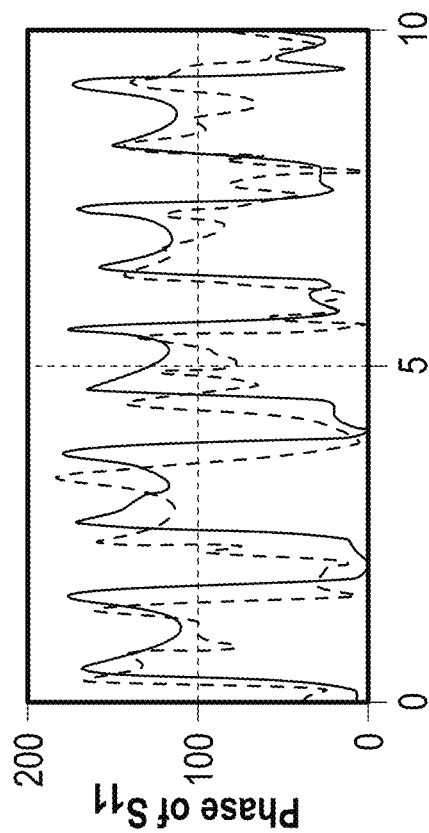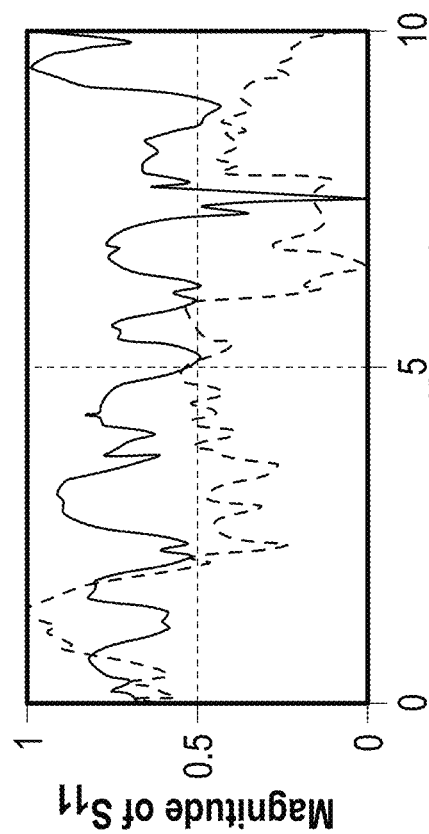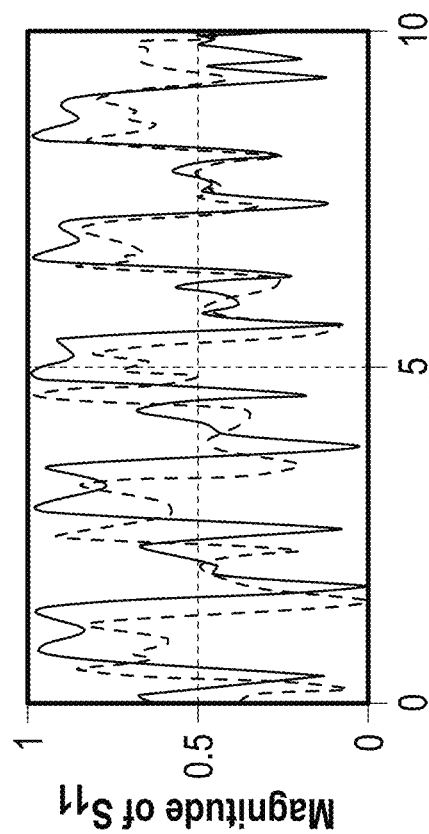
FIG. 14C
FIG. 15C
FIG. 14D
FIG. 15D

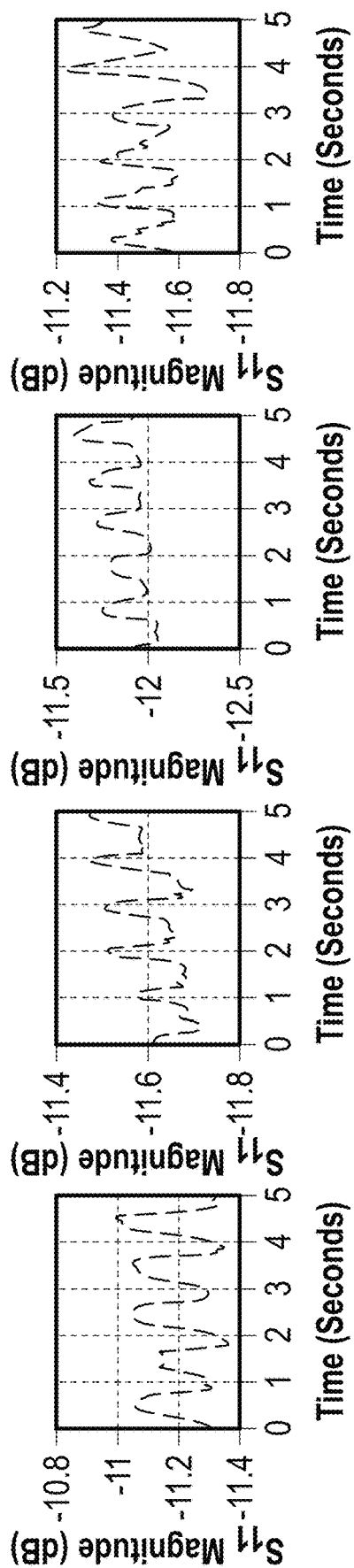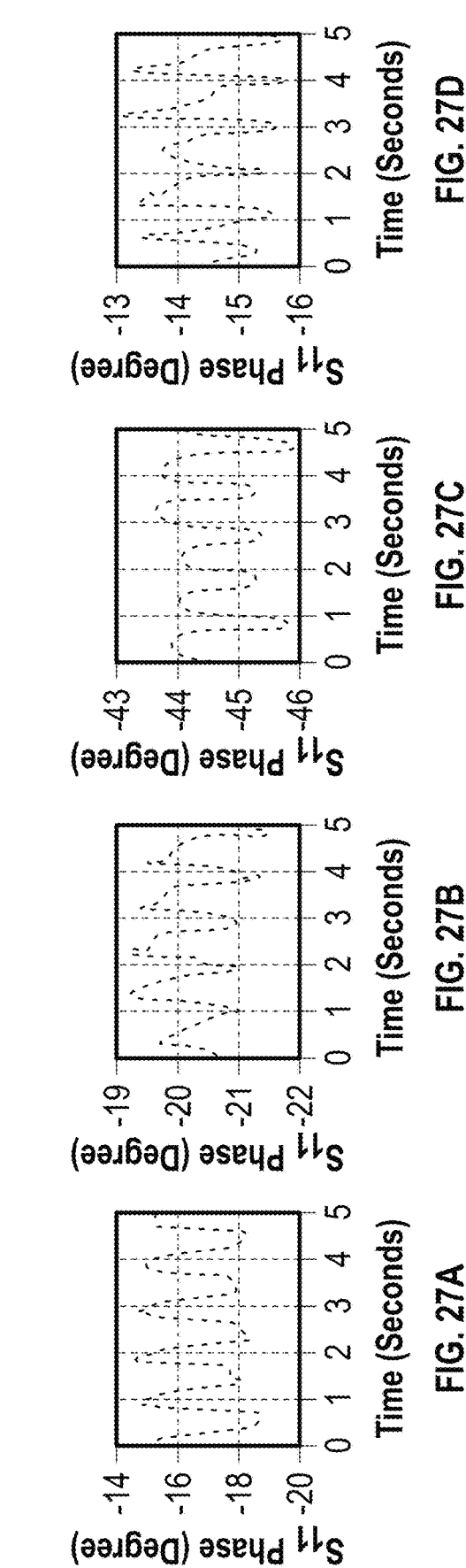

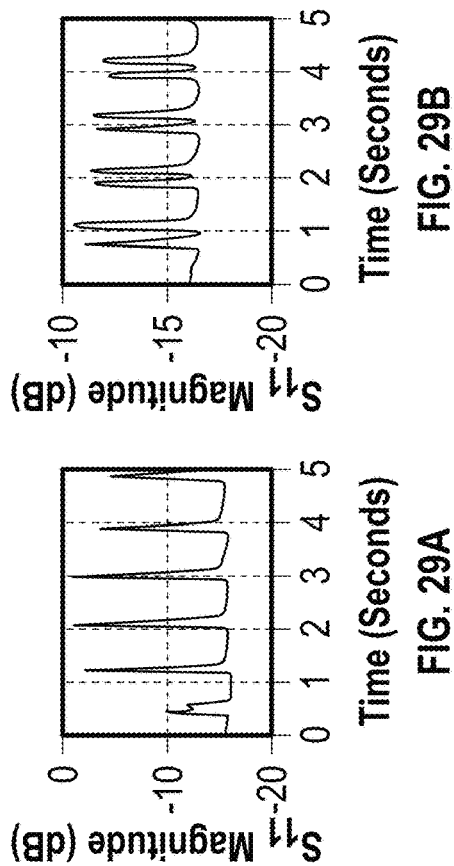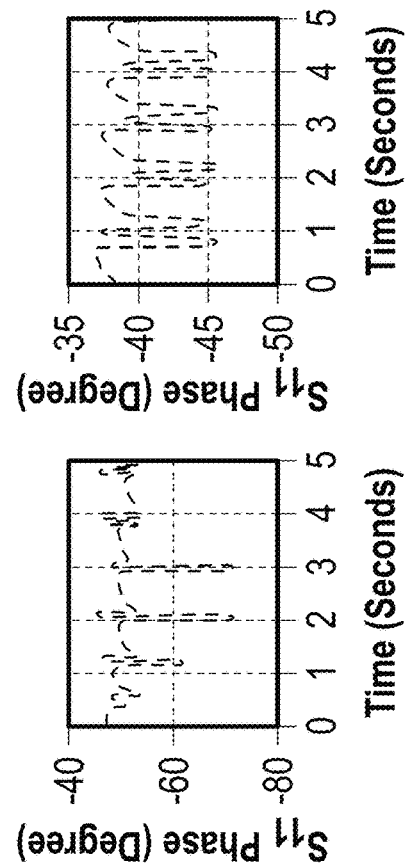

SYSTEM AND METHOD FOR CLASSIFICATION OF BODY ACTIVITIES WITH ON-BODY ANTENNA REFLECTION COEFFICIENT

CROSS REFERENCE TO RELATED APPLICATIONS

This applications claims the benefit of U.S. Provisional Patent Application Ser. No. 62/352,808, filed Jun. 21, 2016, and U.S. Provisional Patent Application Ser. No. 62/468,148 filed Mar. 7, 2017, which are incorporated by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to classification of body activities through wireless transmission. More specifically, the disclosure relates to the classification of body activities through measurements in changes of reflected power and resulting changes in antenna reflection coefficients with the activities.

Description of the Related Art

The classification and resultant monitoring of body activities has a number of important applications in preventive healthcare, biomechanics research, sports science, computer gaming, and security surveillance. Until now, the most accurate activity recognition method has been based on optical activity-capture system, which utilizes multiple cameras to track body movements from different viewing angles. However, this approach is restricted to laboratory environment and requires an expensive equipment setup as well as careful camera calibrations. Tracking a human-subject activity in daily lives using a wearable system is desirable for activity recognition. Miniaturized wearable sensors consisting of accelerometers, gyroscopes, and magnetometers have been developed. Experimental trials have shown that many activities can be distinguished with satisfactory classification accuracy.

Further, monitoring hand and finger motions has long been of interests because of their important applications in human-computer interfacing, virtual control, computer gaming, and biomechanics research, and so forth. For example, if hand and finger motions can be accurately recognized from a remote distance, they can provide convenience and flexibility to users. They could be used in small-sized electronic devices, instead of employing a small button. In particular, controlling a handheld device using clicking, scrolling, and zooming motions without contacting a touchscreen can offer a new scheme of operating a portable device. Traditionally, hand- and finger-gesture recognitions have been addressed in terms of image and video processing by analyzing the time-varying motion of the hand. Another alternate approach is to utilize a radar system, which can operate regardless of the light condition. In addition, micro-Doppler signatures have been investigated for hand-gesture recognition. One particular challenge of the Doppler radar approach is that the beam of the radar antenna must be directed to the target to receive responses from the target.

More recently, researchers have exploited the use of an on-body wireless channel to classify human activities using at least two antennas to measure changes in a transmission power and resulting transmission coefficients between the antennas during the activities. Transmitting and receiving antennas are placed on different parts of a human body (e.g., wrist and waist), and the transmission channel between two antennas is recorded while a subject performs daily activities. For a fixed transmission power, the receiving signal strength exhibits unique time-varying features for different activities in a transmission coefficient, which can be used for activity-recognition purposes. This on-body wireless channel method is more power-efficient and low cost, because it does not rely on specialized physical sensors such as accelerometers that also require a wireless channel to transmit data. However, the transmission power measurements between the at least two antennas requires power consumptions of multiple antennas. Further, it is known that autonomic internal functions, such as heartbeat and respiration, are known to cause some perturbances in near-reactive fields of an on-body antenna. Other types of sensors, such as accelerometer and gyroscope sensors have been used to identify arm, hand, and finger gestures with substantial accuracy. Surface-mounted electromyogram sensors have also been utilized to classify gestures by collecting the electrical signal generated by muscle activities. However, these physical sensors need to be integrated into wireless wearable devices, which increases cost and overall power consumption.

Therefore, there remains a need for an improved system to measure and classify body activities having activities through wireless transmissions.

BRIEF SUMMARY OF THE INVENTION

The present disclosure provides a system and method for classifying body activities through an on-body antenna measuring changes in reflected power and the resulting reflection coefficients, in contrast to two antenna systems that measure transmission power therebetween. A single on-body antenna can be attached or held in close proximity to the body. The antenna can be calibrated based on changes in the reflection coefficients for various calibration activities for the location at which the antenna is placed on the body. Magnitude changes and patterns of the reflection coefficients at a given frequency for a given activity can be compared with calibrated data to correlate a given activity. Further accuracy can be gained by comparing both magnitude and phase changes and patterns at a given frequency with calibrated data for a given activity. The antenna can use power losses from a transmitted signal to measure the changes in the reflected power to minimize power requirements.

The disclosure provides a method of electronically classifying an activity of a body, comprising: electronically measuring reflected power with an antenna coupled to the body; processing the measured reflected power to create data to establish a pattern for the body activity; comparing the pattern with known patterns for known body activities; and electronically classifying the activity based on a correlation of the pattern with a known pattern.

The disclosure also provides a system for classifying activities of a body, comprising: an antenna having a transmitter and a receiver which receive data from the antenna transmitter on reflected power from the body during body activities and the antenna having a near-field region sensitive to reflected power from the transmitter, the antenna located on the body and configured to send data on the reflected power as measurements; a receiver electromagnetically coupled with the antenna to receive signals from the antenna on the measurements; a processor configured to determine changes in reflected power and transform the reflected power measurements into data of reflection coefficients; and a memory to store reflected power measurements from the body activities, reflection coefficients, or a combination thereof.

BRIEF DESCRIPTION OF THE SEVERAL VIEWS OF THE DRAWINGS

FIG. 12A is a chart that shows an exemplary pattern of the reflection coefficient magnitude for the activity shown in FIG. 11A, measured at 433 MHz when the antenna was placed on the chest.

FIG. 12B is a chart that shows an exemplary pattern of the reflection coefficient magnitude for the activity shown in FIG. 11B, measured at 433 MHz when the antenna was placed on the chest.

FIG. 12E is a chart that shows an exemplary pattern of the reflection coefficient magnitude for the activity shown in FIG. 11E, measured at 433 MHz when the antenna was placed on the chest.

FIG. 12F is a chart that shows an exemplary pattern of the reflection coefficient magnitude for the activity shown in FIG. 11F, measured at 433 MHz when the antenna was placed on the chest.

FIG. 13A is a chart that shows an exemplary pattern of the reflection coefficient phase for the activity shown in FIG. 11A, measured at 433 MHz when the antenna was placed on the chest.

FIG. 13B is a chart that shows an exemplary pattern of the reflection coefficient phase for the activity shown in FIG. 11B, measured at 433 MHz when the antenna was placed on the chest.

FIG. 13E is a chart that shows an exemplary pattern of the reflection coefficient phase for the activity shown in FIG. 11E, measured at 433 MHz when the antenna was placed on the chest.

FIG. 13F is a chart that shows an exemplary pattern of the reflection coefficient phase for the activity shown in FIG. 11F, measured at 433 MHz when the antenna was placed on the chest.

FIG. 14C is a chart that shows an exemplary pattern of the reflection coefficient magnitude for the activity shown in FIG. 11C, measured at 433 MHz when the antenna was placed on the right wrist.

FIG. 14D is a chart that shows an exemplary pattern of the reflection coefficient magnitude for the activity shown in FIG. 11D, measured at 433 MHz when the antenna was placed on the right wrist.

FIG. 15C is a chart that shows an exemplary pattern of the reflection coefficient phase for the activity shown in FIG. 11C, measured at 433 MHz when the antenna was placed on the right wrist.

FIG. 15D is a chart that shows an exemplary pattern of the reflection coefficient phase for the activity shown in FIG. 11D, measured at 433 MHz when the antenna was placed on the right wrist.

FIG. 26A is a chart that shows an exemplary pattern of the reflection coefficient magnitude for the activity shown in FIG. 23A, measured at the resonant frequency for the type B antenna on the left wrist.

FIG. 26B is a chart that shows an exemplary pattern of the reflection coefficient magnitude for the activity shown in FIG. 23B, measured at the resonant frequency for the type B antenna on the left wrist.

FIG. 26C is a chart that shows an exemplary pattern of the reflection coefficient magnitude for the activity shown in FIG. 23C, measured at the resonant frequency for the type B antenna on the left wrist.

FIG. 26D is a chart that shows an exemplary pattern of the reflection coefficient magnitude for the activity shown in FIG. 23D, measured at the resonant frequency for the type B antenna on the left wrist.

FIG. 27A is a chart that shows an exemplary pattern of the reflection coefficient phase for the activity shown in FIG. 23A, measured at the resonant frequency for the type B antenna on the left wrist.

FIG. 27B is a chart that shows an exemplary pattern of the reflection coefficient phase for the activity shown in FIG. 23B, measured at the resonant frequency for the type B antenna on the left wrist.

FIG. 27C is a chart that shows an exemplary pattern of the reflection coefficient phase for the activity shown in FIG. 23C, measured at the resonant frequency for the type B antenna on the left wrist.

FIG. 27D is a chart that shows an exemplary pattern of the reflection coefficient phase for the activity shown in FIG. 23D, measured at the resonant frequency for the type B antenna on the left wrist.

FIG. 29A is a chart that shows an exemplary pattern of the reflection coefficient magnitude for the activity shown in FIG. 28A, measured at the resonant frequency for the type A antenna on the left wrist.

FIG. 29B is a chart that shows an exemplary pattern of the reflection coefficient magnitude for the activity shown in FIG. 28B, measured at the resonant frequency for the type A antenna on the left wrist.

FIG. 29C is a chart that shows an exemplary pattern of the reflection coefficient magnitude for the activity shown in FIG. 28C, measured at the resonant frequency for the type A antenna on the left wrist.

FIG. 29D is a chart that shows an exemplary pattern of the reflection coefficient magnitude for the activity shown in FIG. 28D, measured at the resonant frequency for the type A antenna on the left wrist.

FIG. 30A is a chart that shows an exemplary pattern of the reflection coefficient phase for the activity shown in FIG. 28A, measured at the resonant frequency for the type A antenna on the left wrist.

FIG. 30B is a chart that shows an exemplary pattern of the reflection coefficient phase for the activity shown in FIG. 28B, measured at the resonant frequency for the type A antenna on the left wrist.

FIG. 30C is a chart that shows an exemplary pattern of the reflection coefficient phase for the activity shown in FIG. 28C, measured at the resonant frequency for the type A antenna on the left wrist.

FIG. 30D is a chart that shows an exemplary pattern of the reflection coefficient phase for the activity shown in FIG. 28D, measured at the resonant frequency for the type A antenna on the left wrist.

DETAILED DESCRIPTION

Figure 1:
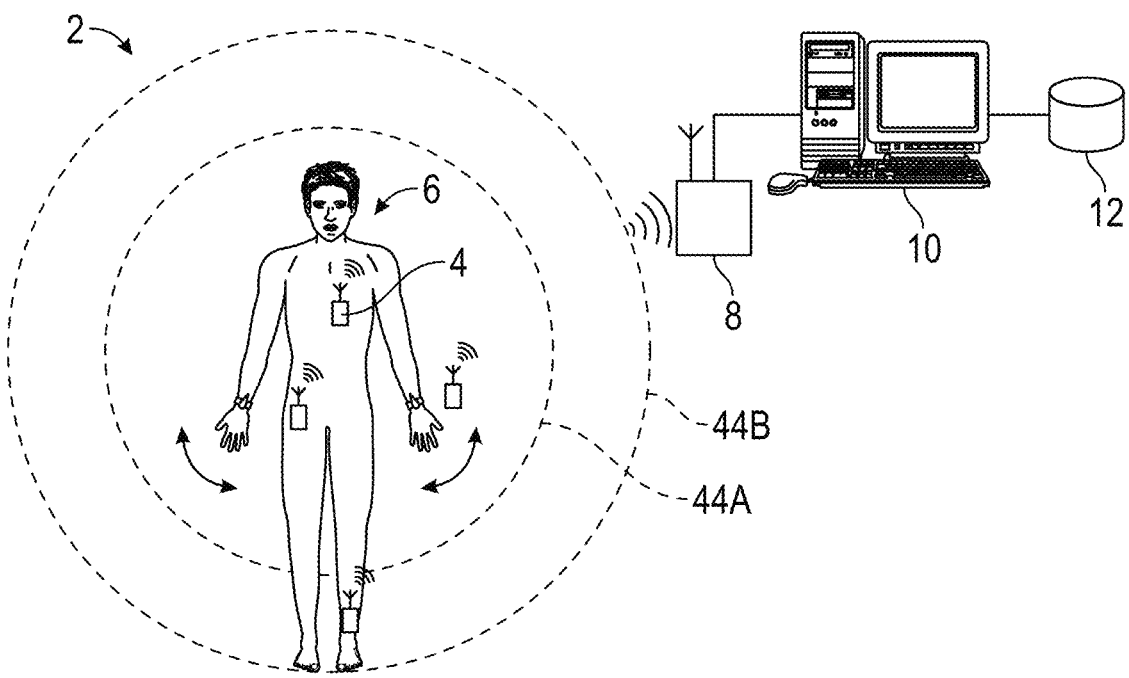
FIG. 1 is a schematic view of an exemplary on-body antenna system with a subject.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a processor would encompass a processing system of related components that are known to those with ordinary skill in the art and may not be specifically described.

The present disclosure provides a system and method for classifying body activities through an on-body antenna measuring changes in reflected power and the resulting reflection coefficients, in contrast to two antenna systems that measure transmission power therebetween. A single on-body antenna can be attached or held in close proximity to the body. The antenna can be calibrated based on changes in the reflection coefficients for various calibration activities for the location at which the antenna is placed on the body. Magnitude changes and patterns of the reflection coefficients at a given frequency for a given activity can be compared with calibrated data to correlate a given activity. Further accuracy can be gained by comparing both magnitude and phase changes and patterns at a given frequency with calibrated data for a given activity. The antenna can use power losses from a transmitted signal to measure the changes in the reflected power to minimize power requirements.

FIG. 1 is a schematic view of an exemplary on-body antenna system with a subject. An on-body antenna system 2 includes an on-body antenna 4 that can coupled to the body of a subject 6 by being placed on or in close proximity to a subject. The antenna 4 can be placed on a variety of locations on the subject. For example and without limitation, the antenna can be placed on the chest, around the waist, on the wrist, ankle, and other locations. The antenna can be calibrated for the particular location to classify the body activities. The term "body activity" or "body activities" is used broadly herein and is intended to include volitional and accidental movements, such as movements of the head, face including eyes, chest, torso, upper limb movements, such as arms, wrists, hands, and fingers, lower limb movements, such as legs, toes, ankles, and feet, and the like. Such movements can indicate or be used to determine possible reasons for such movements such as moods, reactions to external stimuli or conditions such as falls. The term "antenna" is used broadly herein to include a receiver and/or transmitter, such as a transceiver, a power supply, such as a battery, and associated components to receive and/or transmit signals, and optionally display results at the antenna. In at least one embodiment, the antenna 4 can include a handheld or smaller transceiver with capable of receiving signals and transmitting signals wirelessly. The on-body antenna has a near-field region 44A for sensing changes in the reflected power and measurement thereof. The reflected power can be used to provide the resulting reflection coefficient. For purposes herein, measurement of the reflected power includes measurement of parameters related to reflected power, such as measurements of antenna impedance and the like to classify the body activities. In the near-field region, absorption of radiation affects the load on the transmitter and the propagation of electromagnetic waves has interference because of reflected power. The size of the near-field region varies, depending on the antenna frequency used. A higher frequency has a smaller region 44A and a lower frequency has a larger region 44B. A second antenna 8 can be placed remotely to the antenna 4 but with sufficient proximity to receive wireless transmissions and optionally to transmit wirelessly to the antenna 4. The antenna 8 can be coupled to an electronic processing device 10, such as a computer, server, mainframe, tablet, smart phone, and the like. The processing device 10 can be coupled to a database 12, internally or externally to the device 10. The database 12 can store data exhibiting patterns and other identifying data used to classify the body activities. The antenna 8 can provide information received from the antenna 4 to the processing device 10. The processing device 10 can process the incoming data through the antenna 8 from the antenna 4 and generate data corresponding to patterns for known body activities and compare such patterns with further activities to classify the further activities.

Figure 2:
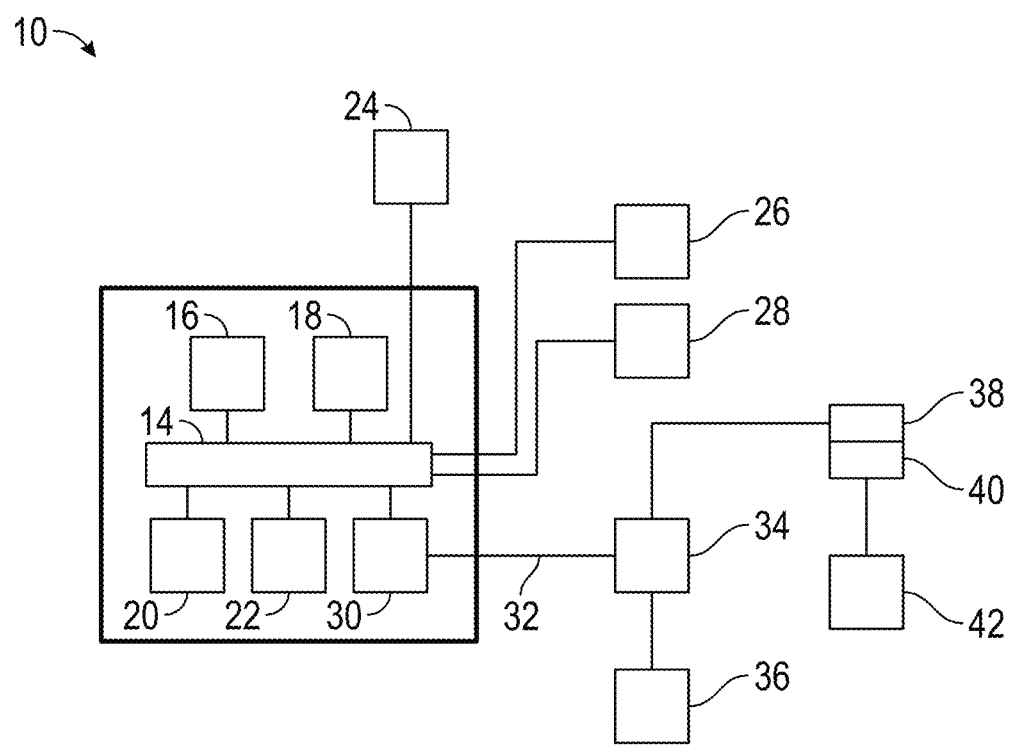
FIG. 2 is a schematic block diagram of an exemplary processor device used for measurement and correlation of data.

FIG. 2 is a schematic block diagram of an exemplary processor device used for measurement and correlation of data. FIG. 2 illustrates the electronic processing device of FIG. 1 in more detail according to the disclosed embodiments. According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Such a processing device 10 typically includes a bus 14 or other communication mechanism for communicating information and a processor 16 coupled with the bus 14 for processing information. The processing device 10 may also include a main memory 18, such as a random access memory (RAM) or other dynamic storage device, coupled to the bus 14 for storing computer-readable instructions to be executed by the processor 16. The main memory 18 may also be used for storing temporary variables or other intermediate information during execution of the instructions to be executed by the processor 16. The processing device 10 may further include a read-only memory (ROM) 20 or other static storage device coupled to the bus 14 for storing static information and instructions for the processor 16. A computer-readable storage device 22, such as a magnetic, optical, or solid state device, may be coupled to the bus 14 for storing information and instructions for the processor 16.

The processing device 10 may be coupled via the bus 14 to a display 24, such as a liquid crystal display (LCD) or a light emitting diode (LED) display, for displaying information to a user. An input device 26, including, for example, alphanumeric and other keys, voice systems, screen touch systems, and other input systems may be coupled to the bus 14 for communicating information and command selections to the processor 16. Another type of user input device may be a cursor control 28, such as a mouse, a trackball, or cursor direction keys for communicating direction information and command selections to the processor 16, and for controlling cursor movement on the display 24. The cursor control 28 generally has two degrees of freedom in two axes, a first axis (e.g., X axis) and a second axis (e.g., Y axis), that allow the device to specify positions in a plane, but can include three axes for spatial positions.

The term "computer-readable instructions" as used above refers to any instructions that may be performed by the processor 16 and/or other components. Similarly, the term "computer-readable medium" refers to any storage medium that may be used to store the computer-readable instructions. Such a medium may take many forms, including, but not limited to, non-volatile media, volatile media, and transmission media. Non-volatile media may include, for example, optical or magnetic disks, such as the storage device 22. Volatile media may include dynamic memory, such as main memory 18. Transmission media may include coaxial cables, copper wire and fiber optics, including wires of the bus 14. Common forms of computer-readable media may include, for example, a floppy disk, a flexible disk, hard disk, magnetic tape, any other magnetic medium, a CD ROM, DVD, any other optical medium, punch cards, paper tape, any other physical medium with patterns of holes, a RAM, a PROM, an EPROM, a FLASH EPROM, any other memory chip or cartridge, or any other medium from which a computer may read.

Various forms of the computer-readable media may be involved in carrying one or more sequences of one or more instructions to the processor 16 for execution. For example, the instructions may initially be borne on a magnetic disk of a remote computer. The remote computer may load the instructions into its dynamic memory and send the instructions over a telephone line using a modem. A modem local to the processing device 10 may receive the data on the telephone line and use an infrared transmitter to convert the data to an infrared signal. An infrared detector coupled to the bus 14 may receive the data carried in the infrared signal and place the data on the bus 14. The bus 14 carries the data to the main memory 18, from which the processor 16 retrieves and executes the instructions. The instructions received by the main memory 18 may optionally be stored on the storage device 22 either before or after execution by the processor 16.

The computer system 10 also includes a communication interface 30 coupled to the bus 14. The communication interface 30 provides a two-way data communication coupling to a network link 32 that is connected to a local network 34. For example, the communication interface 30 may be an integrated services digital network (ISDN) card, cable modem, satellite modem, or a modem to provide a data communication connection to a corresponding type of telephone line. As another example, the communication interface 30 may be a local area network (LAN) card to provide a data communication connection to a compatible LAN. Wireless links may also be implemented. Generally, the communication interface 30 can send and receive electrical, electromagnetic, or optical signals that carry digital data streams representing various types of information.

The network link 32 generally provides data communication through one or more networks to other data devices. For example, the network link 32 may provide a connection through local network 34 to a host computer 36 or to data equipment operated by an Internet Service Provider (ISP) 38. The ISP 38 in turn provides data communication services through the world wide packet data communication network now commonly referred to as the "Internet" 40. The local network 34 and the Internet 40 both use electrical, electromagnetic or optical signals that carry digital data streams. The signals through the various networks and the signals on the network link 32 and through the communication interface 30, which carry the digital data to and from computer system 10, are example forms of transmission media.

The computer system 10 can send messages and receive data, including program code, through the network(s), network link 32 and communication interface 30. In the Internet example, a server 42 might transmit a requested code for an application program through Internet 40, ISP 38, local network 34 and communication interface 30. The received code may be executed by the processor 16 as it is received, and/or stored in the storage device 22, or other non-volatile storage for later execution.

Figure 3:
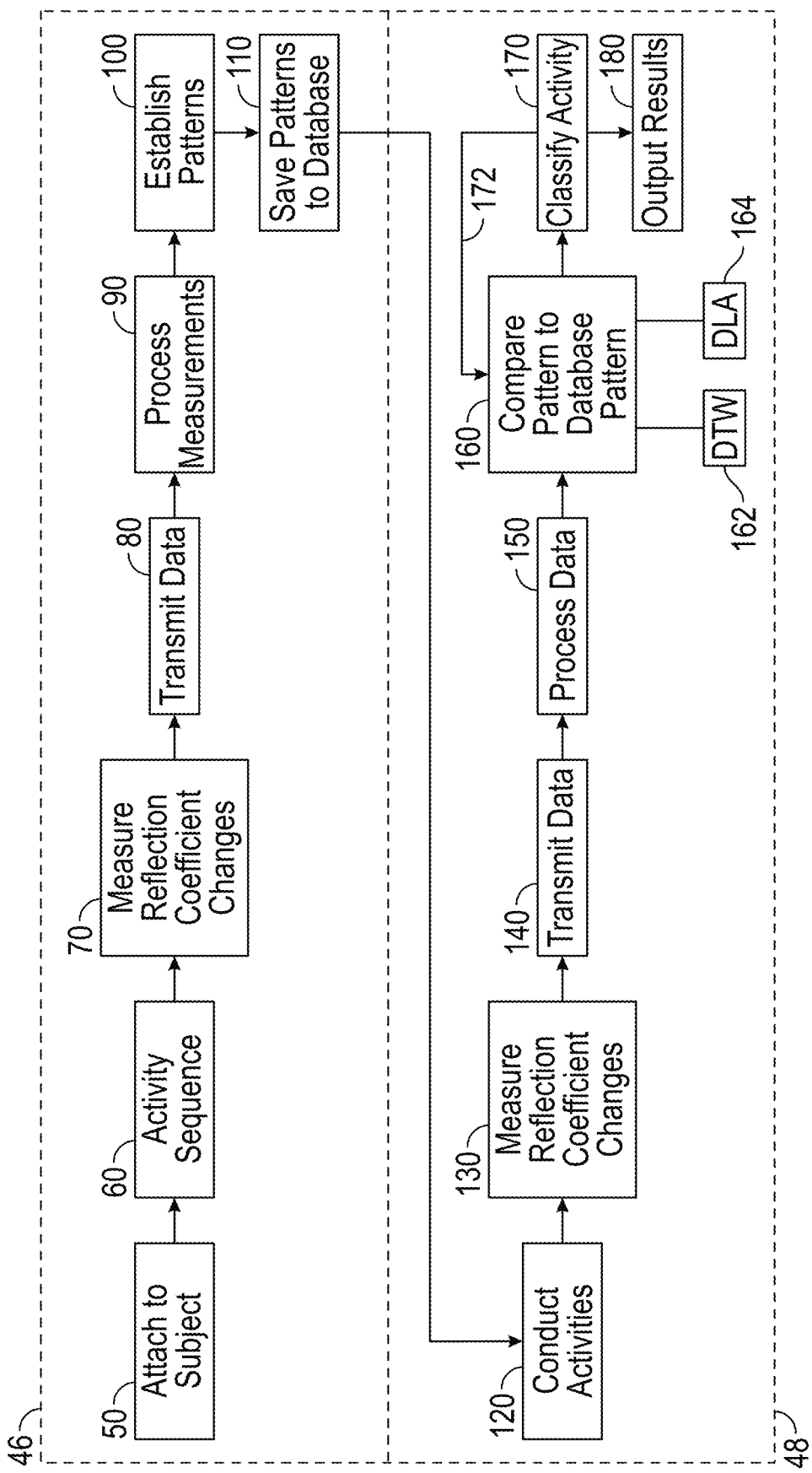
FIG. 3 is a schematic flow chart of an exemplary process for using the on-body antenna system.

FIG. 3 is a schematic flow chart of an exemplary process for using the on-body antenna system. The flowchart covers a calibration sequence 46 of a given location of the antenna for known body activities, and a classification sequence 48 of measurement of further body activities that can be compared to the calibrated activities to classify the further activities. In some circumstances, both sequences will be used. In some circumstances such as when the calibration has already occurred or when a pre-loaded database of typical body activities is used, the classification sequence for further activities can be used.

Block 50 includes attaching the on-body antenna to the subject to be measured. The subject is generally a human, although other mammals and other living creatures can be used. The attachment location can vary. Advantageously, the attachment location is in an approximate central area of the body activities. For example, the antenna could be located along the body between the arms and legs. Because the on-body antenna has the near-field region that depends on frequency for size and sensitivity, certain locations on the body may be preferred for some embodiments. For example, to improve accuracy for general body activities involving multiple movements of arms, legs, and head, the antenna can be placed on the waist, chest, wrist, and other locations. In some embodiments, the ankle, head, feet, or legs may be more appropriate, for example, if a goal is to focus on the lower body activities, where measurement may be affected by the size of the near field region. In other embodiments, the wrist or fingers may be appropriate, for example, if a goal is to focus on wrist, hand, or finger movements. An antenna can be coupled to a watch or strap around the wrist and be used for wrist and finger movements. In still another embodiment, the head or face may be appropriate, for example, if a goal is to focus on head or facial movements. An antenna can be coupled to part of the head, such as an ear, and be used for head and neck movements. An antenna can be coupled to the front of the face and be used for eye movements. The locations are exemplary and without limitation.

For the calibration sequence 46, the subject can move through known body activities in block 60. Because the reflected power and therefore reflection coefficient varies depending upon the antenna location, a calibration is useful to establish data for given body activities for later use in classifying further body activities. The known body activities and measurements of the reflected power for the selected location of the on-body antenna can be used to establish the data as known patterns useful for classification of further and perhaps unknown activities. As the subject moves through the known body activities, the antenna can measure reflection coefficient changes in block 70. The data can be transmitted to the receiver 8 and sent to the computer system 10 in block 80. The computer 10 can process the measurements in block 90, and establish sets of data as electronic patterns in block 100. The data for the patterns can be stored in the database as a data set for subsequent reference in block 110.

For the classification sequence 48, the subject 6 can perform activities in any order or sequence, with variations in styles, and otherwise as appropriate in block 120. The antenna 4 can measure changes in the reflected power as the movement occurs in block 130. The antenna can transmit the data from the measurements to the receiver 8 in block 140. The data can be sent to the computer system 10 for processing the data in block 150, including possibly determining the reflection coefficients from the reflected power measurements. The processing can generate data that may include averaging, normalizing, and other steps that may be appropriate to process the data for a pattern. Because the data is measured in various frequencies, the data will have a magnitude and a phase angle. The data can include processing the magnitude of the changes in the reflection coefficient, the phase of the reflection coefficient changes, or a combination thereof. For increased accuracy, the magnitude and phase angles can be processed for a given data set. The processed data from block 150 can be compared to the calibration data in block 160. The calibration data encompasses patterns derived from the measurements of known activities. The data of the patterns from the further activities in block 120, can be compared to the patterns in the calibrated data in block 110.

Because of the variability in complexity and the temporal nature of the data that can vary in speed in measuring the data and establishing the patterns, special algorithms (herein "time-varying algorithms") may be helpful in block 160 of comparing the data patterns of the known activities to the data patterns of the further activities. These algorithms can analyze the data patterns related to the reflected power, including reflection coefficients, antenna impedance, and the like that are indicative of the reflected power and changes thereof. One such algorithm is known as dynamic time warping ("DTW"). DTW has a capability to calculate the degree of similarity between two temporal signals when variations in time and speed exist. DTW offers an advantage in the contemplated comparisons, because body activities have slight variations in time. DTW finds the path that maximizes the local match between two temporal data sets. The sequences are "warped" non-linearly in the time dimension to determine a measure of their similarity independent of certain non-linear variations in the time dimension.

Another algorithm that may be useful in processing the comparisons in block 160 is known as a deep learning algorithm ("DLA"). DLA is also known as deep structured learning, or hierarchical learning, or deep machine learning. DLA can use multiple non-linear transformations and is based on distributed representations. The underlying assumption behind distributed representations is that observed data is generated by the interactions of factors organized in layers. DLA adds an assumption that these layers of factors correspond to layers of abstraction or composition. Through the non-linear transformations in multiple levels, certain patterns may be generated. These patterns can be compared to other patterns for correspondence. Still further, one or more algorithms can be jointly applied.

In block 170, the comparisons generated in block 160 can be used to classify the body activities. The comparisons between the known activities in the database from block 110 when compared to the further activities provide the ability to classify the further activities. The comparison will likely be imperfect due to variations in the data, and so a percentage correlation can be provided. Certain threshold values of correlation can be predetermined to limit the processing time once the threshold value has been reached. In some embodiments, a feedback loop 172 can direct the prior step of comparing the patterns in block 160 to be repeated for further processing, for example, to obtain a closer correlation.

In block 180, the results of the classification can be presented as output. The output can include the percentage of correlation as a metric of how close the correlation appears to be. Charts and graphs and other output used in the comparison can be provided and such charts and graphs can be normalized and otherwise processed for presentation.

Figure 4:
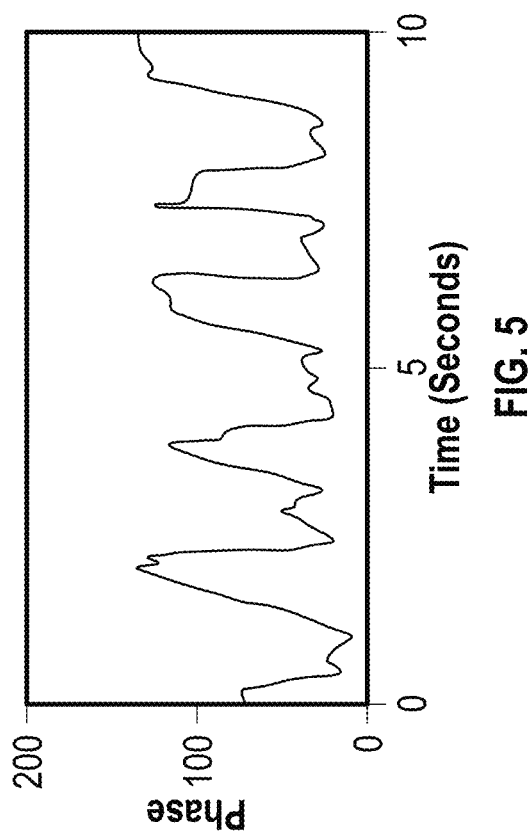
FIG. 4 is a schematic pattern chart of a first type of body activity by magnitude of a reflection coefficient plotted to time.

FIG. 4 is a schematic pattern chart of a first type of body activity by magnitude of a reflection coefficient plotted to time. In this chart, the Y-axis is the reflection coefficient having a maximum value of 1.0 and the X-axis is time measured in seconds. This exemplary pattern is for a known activity such as a single arm swing, using a certain frequency for measuring the reflection coefficient with the antenna 4.

Figure 5:
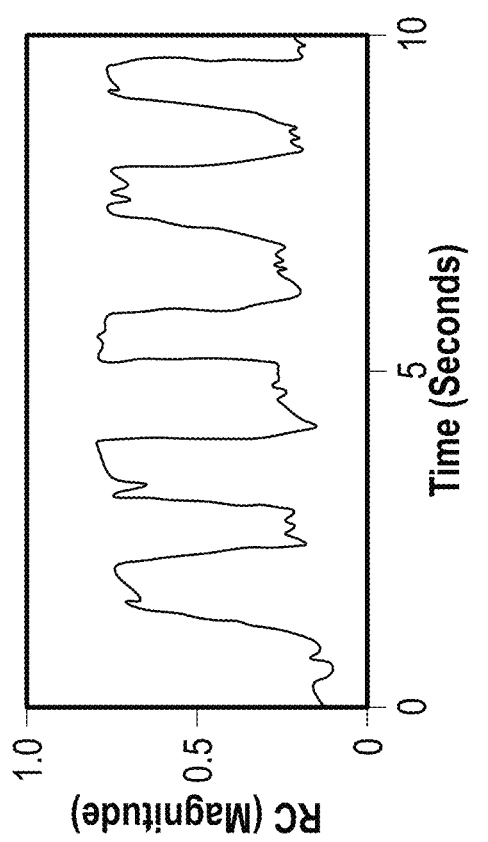
FIG. 5 is a schematic pattern chart of a first type of body activity by phase of the reflection coefficient plotted to time.

FIG. 5 is a schematic pattern chart of a first type of body activity by phase of the reflection coefficient plotted to time. FIG. 5 depicts the Y-axis in units of degrees for the phase of the same single arm activity at the same frequency illustrated in FIG. 4 above and the X-axis is time measured in seconds.

Figure 6:
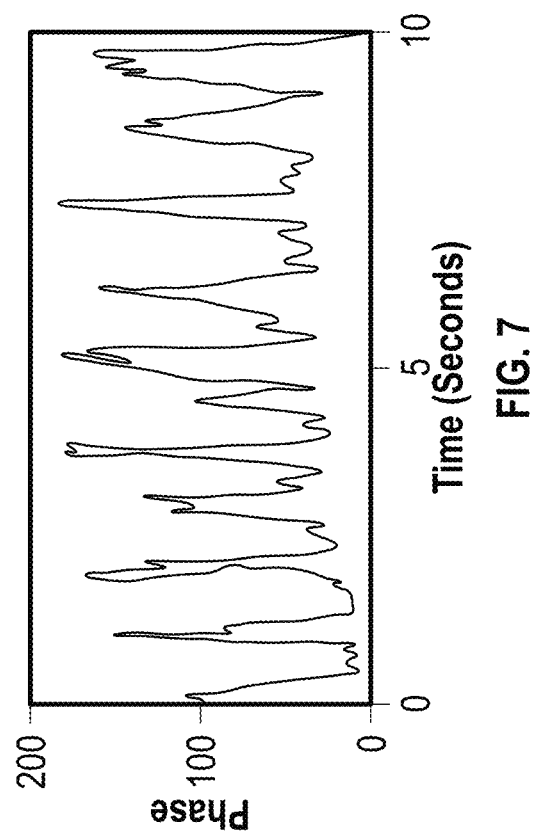
FIG. 6 is a schematic pattern chart of a second type of body activity by magnitude of the reflection coefficient plotted to time.

FIG. 6 is a schematic pattern chart of a second type of body activity by magnitude of the reflection coefficient plotted to time. FIG. 6 is similar in concept to the chart of FIG. 4, but is for a different activity such as both arms swinging, using the same frequency as in FIG. 4.

Figure 7:
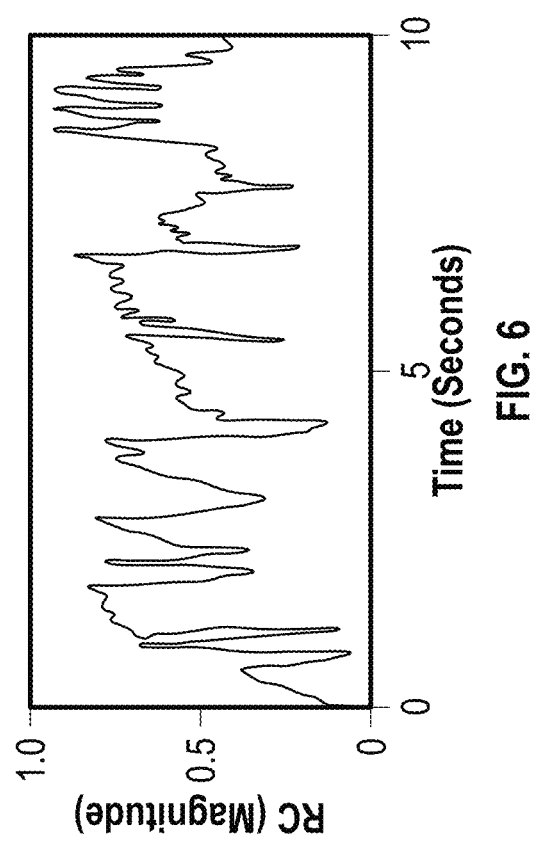
FIG. 7 is a schematic pattern chart of a second type of body activity by phase of the reflection coefficient plotted to time.

FIG. 7 is a schematic pattern chart of a second type of body activity by phase of the reflection coefficient plotted to time. FIG. 7 is similar to the concept of the chart of FIG. 5, but is for a different activity such as both arms swinging, using the same frequency as in FIG. 4.

Figure 8:
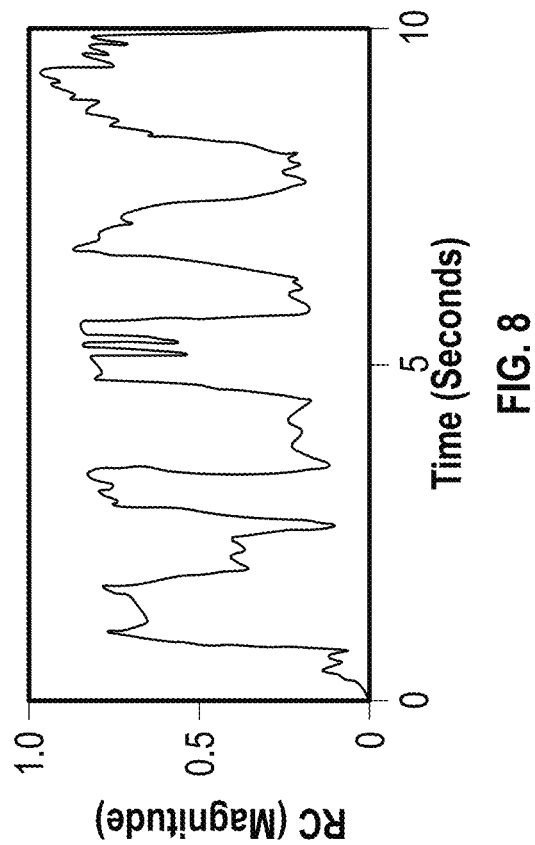
FIG. 8 is a schematic chart of an undetermined activity by magnitude of the reflection coefficient plotted to time.

FIG. 8 is a schematic chart of a further activity by magnitude of the reflection coefficient plotted to time. The further activity produces the changes in the reflected power that is measured with the resulting reflection coefficient. The axes for magnitude and time in FIG. 8 are the same as illustrated in FIG. 4 and FIG. 6. However, the measured pattern varies from both FIG. 4 and FIG. 6.

Figure 9:
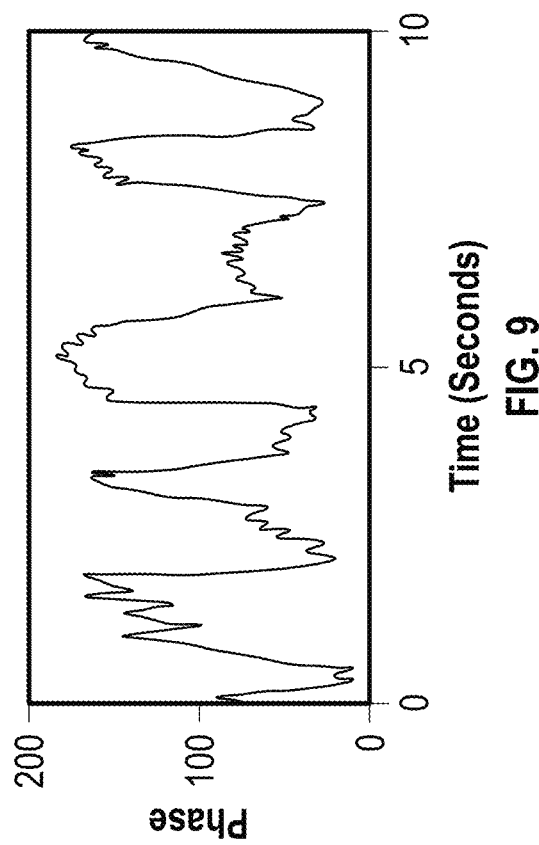
FIG. 9 is a schematic chart of an undetermined activity by phase of the reflection coefficient plotted to time.

FIG. 9 is a schematic chart of an further activity by phase of the reflection coefficient plotted to time. The further activity produces the changes in the reflection coefficient that is measured and processed. The axes for phase and time in FIG. 9 are the same as illustrated in FIG. 5 and FIG. 7. However, the measured pattern varies from both FIG. 5 and FIG. 7.

The patterns of FIG. 8 and FIG. 9 resemble the patterns of FIG. 4 and FIG. 5. A correlation can be calculated by the processor and the value provided to determine whether there is sufficient correlation to classify the further activity in FIG. 8 and FIG. 9 as the known activity in FIG. 4 and FIG. 5.

Experiment 1

Figure 10A:
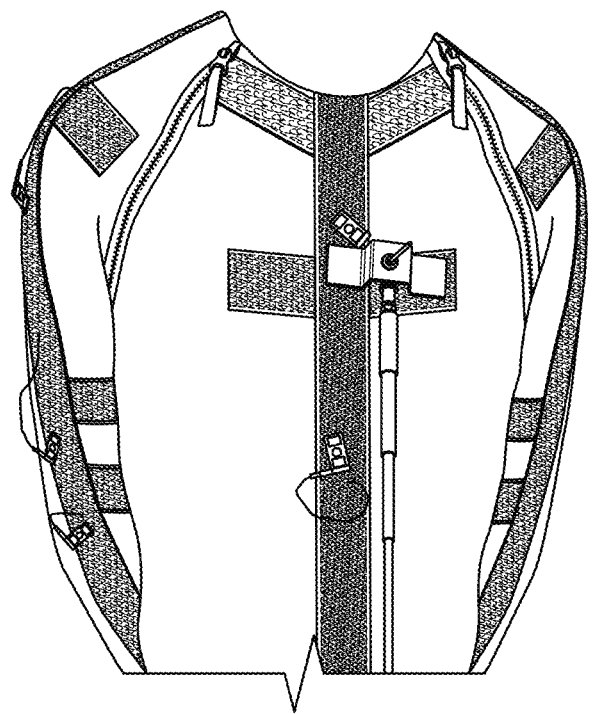
FIG. 10A is an example of a monopole antenna placed on the chest of a subject for measurement of the reflection coefficient.
Figure 10B:
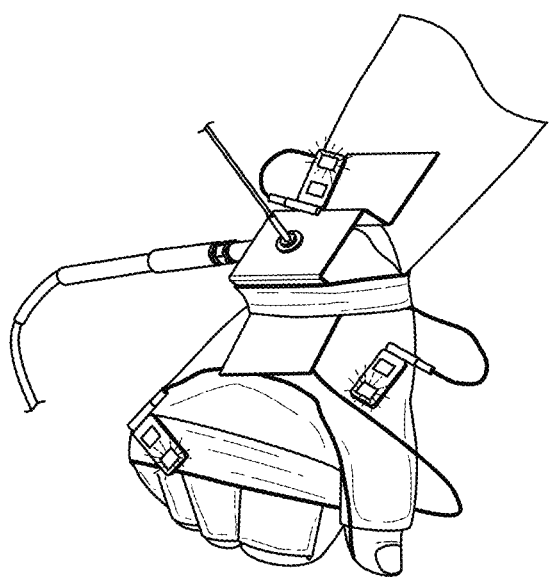
FIG. 10B is an example of a monopole antenna placed on the right wrist of a subject.
Figure 11A:
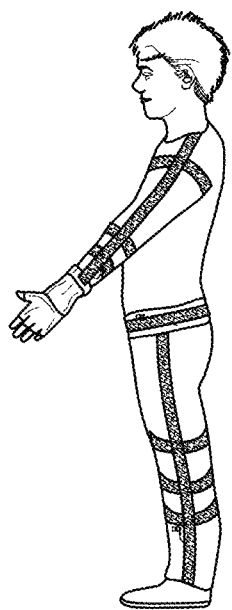
FIG. 11A is an example of a body activity of a single arm swinging.
Figure 11B:
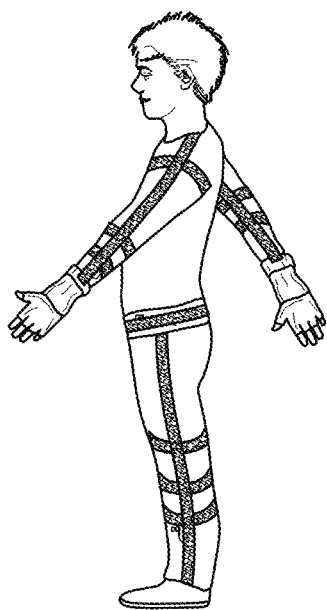
FIG. 11B is an example of a body activity of both arms swinging.
Figure 11C:
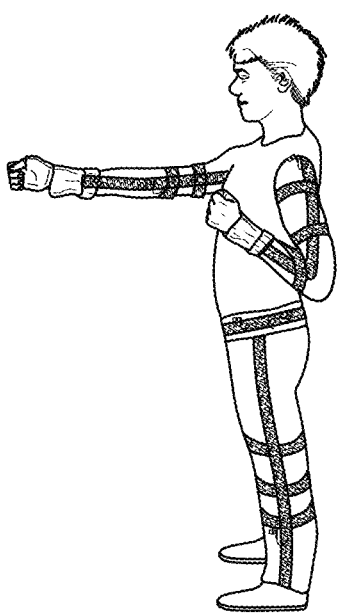
FIG. 11C is an example of a body activity of boxing.
Figure 11D:
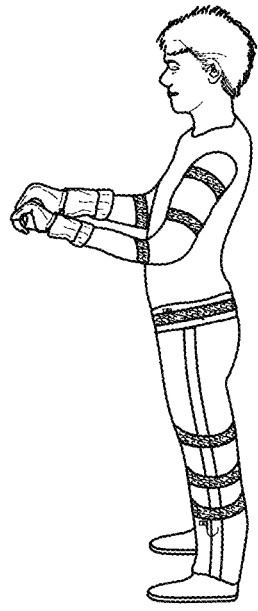
FIG. 11D is an example of a body activity of rowing.
Figure 11E:
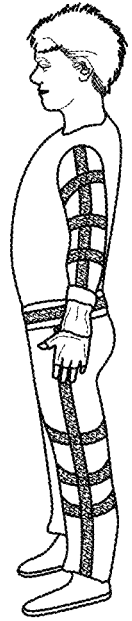
FIG. 11E is an example of a body activity of hopping.
Figure 11F:
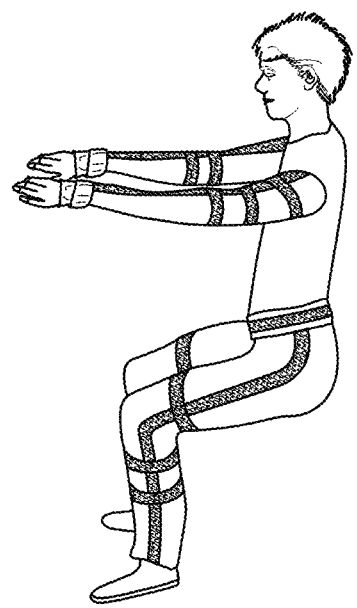
FIG. 11F is an example of a body activity of sitting.
Figure 12C:
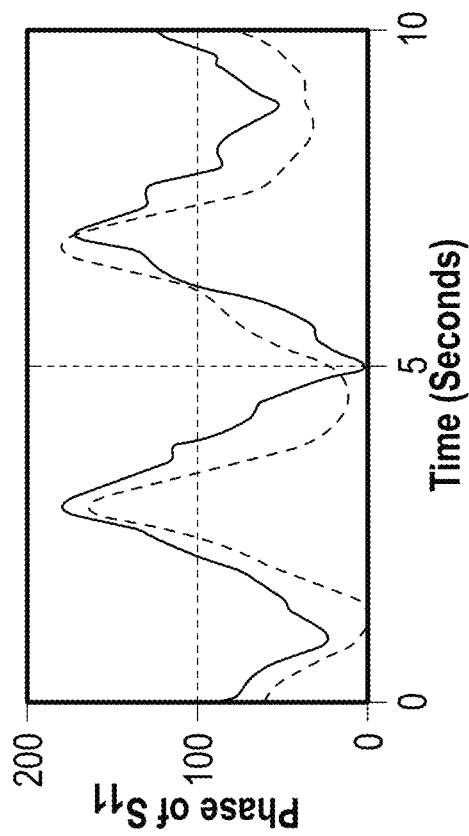
FIG. 12C is a chart that shows an exemplary pattern of the reflection coefficient magnitude for the activity shown in FIG. 11C, measured at 433 MHz when the antenna was placed on the chest.
Figure 12D:
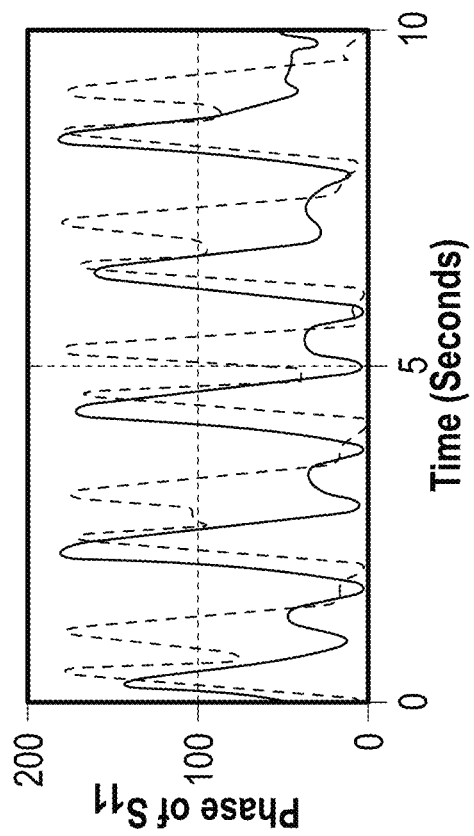
FIG. 12D is a chart that shows an exemplary pattern of the reflection coefficient magnitude for the activity shown in FIG. 11D, measured at 433 MHz when the antenna was placed on the chest.
Figure 13C:
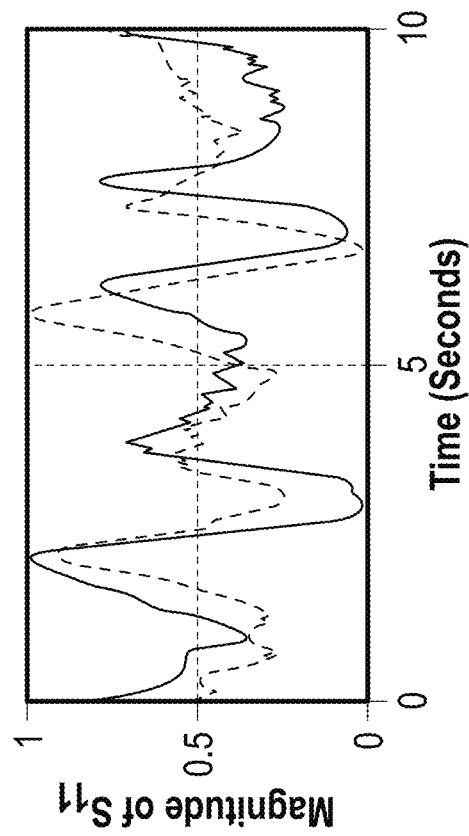
FIG. 13C is a chart that shows an exemplary pattern of the reflection coefficient phase for the activity shown in FIG. 11C, measured at 433 MHz when the antenna was placed on the chest.
Figure 13D:
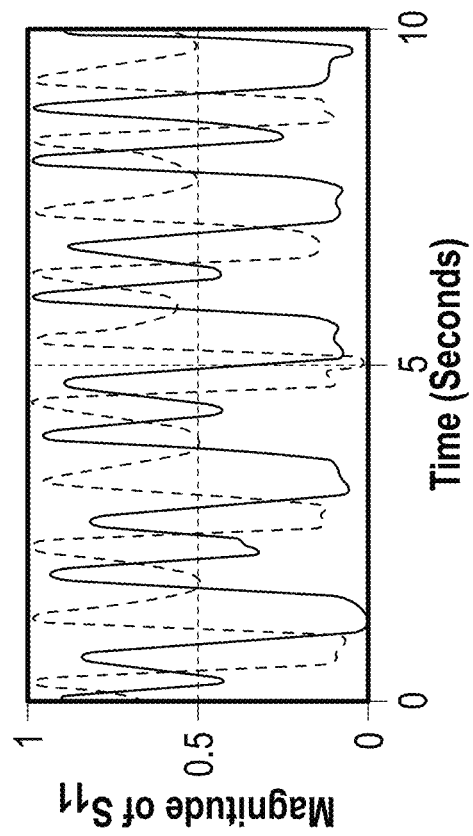
FIG. 13D is a chart that shows an exemplary pattern of the reflection coefficient phase for the activity shown in FIG. 11D, measured at 433 MHz when the antenna was placed on the chest.
Figure 14A:
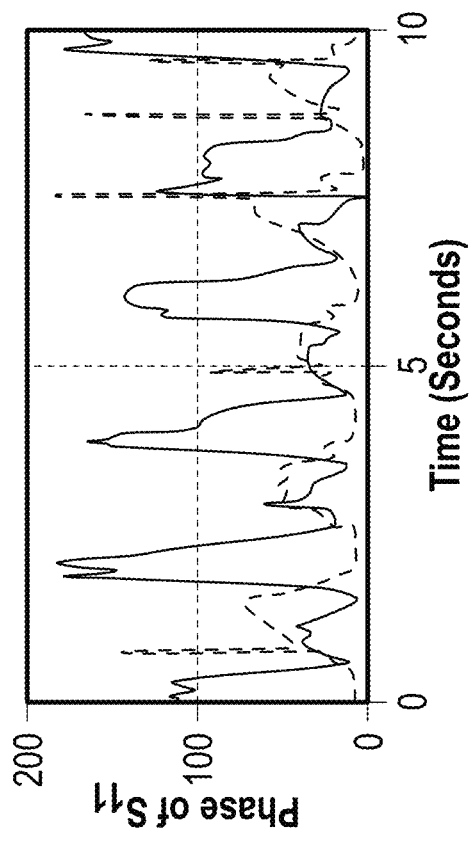
FIG. 14A is a chart that shows an exemplary pattern of the reflection coefficient magnitude for the activity shown in FIG. 11A, measured at 433 MHz when the antenna was placed on the right wrist.
Figure 14B:
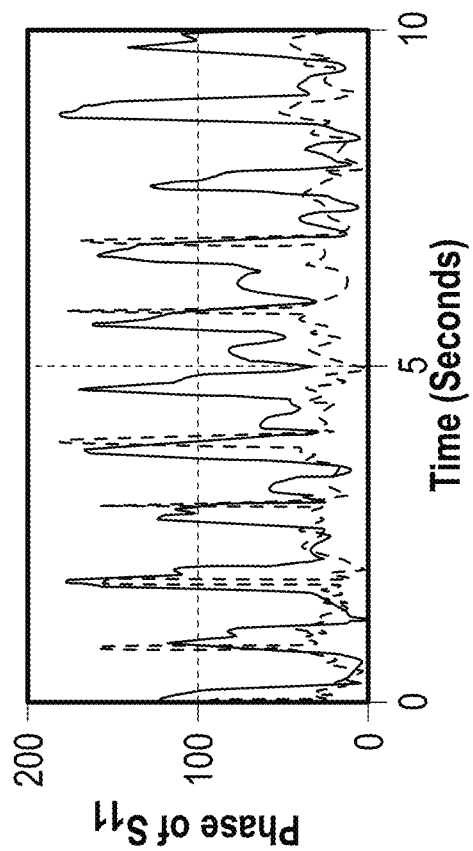
FIG. 14B is a chart that shows an exemplary pattern of the reflection coefficient magnitude for the activity shown in FIG. 11B, measured at 433 MHz when the antenna was placed on the right wrist.
Figure 15A:
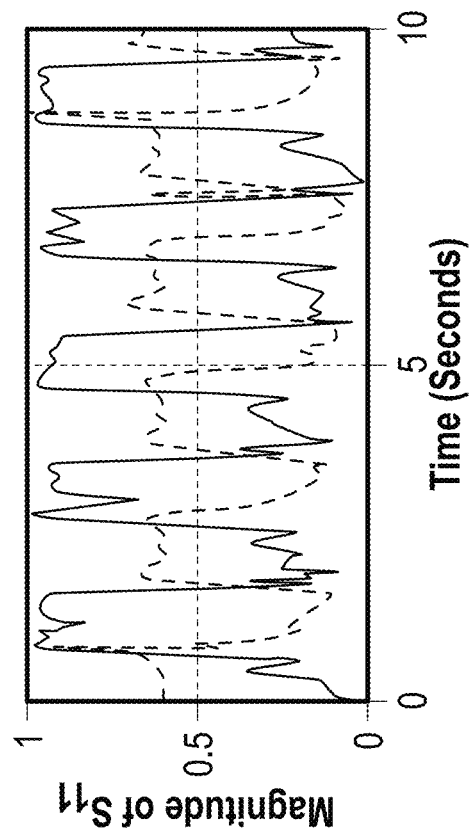
FIG. 15A is a chart that shows an exemplary pattern of the reflection coefficient phase for the activity shown in FIG. 11A, measured at 433 MHz when the antenna was placed on the right wrist.
Figure 15B:
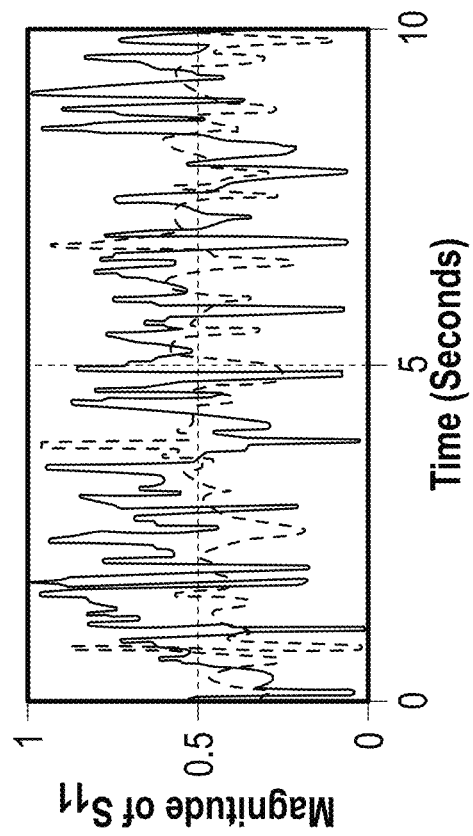
FIG. 15B is a chart that shows an exemplary pattern of the reflection coefficient phase for the activity shown in FIG. 11B, measured at 433 MHz when the antenna was placed on the right wrist.
Figure 14E:
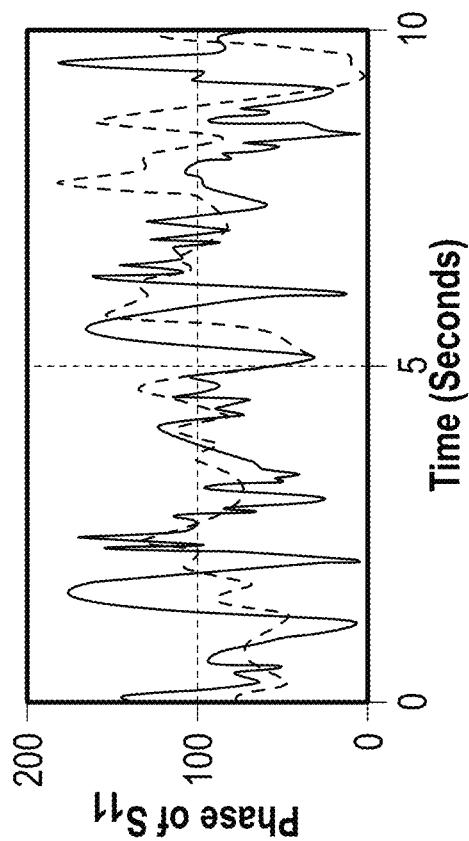
FIG. 14E is a chart that shows an exemplary pattern of the reflection coefficient magnitude for the activity shown in FIG. 11E, measured at 433 MHz when the antenna was placed on the right wrist.
Figure 14F:
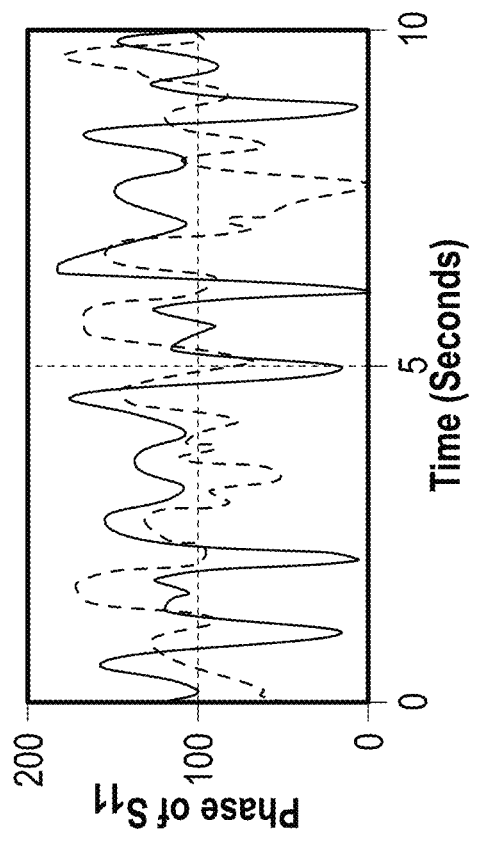
FIG. 14F is a chart that shows an exemplary pattern of the reflection coefficient magnitude for the activity shown in FIG. 11F, measured at 433 MHz when the antenna was placed on the right wrist.
Figure 15E:
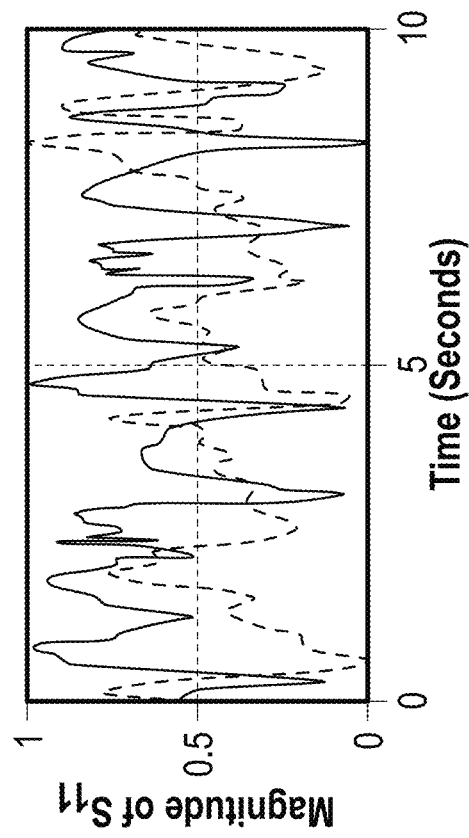
FIG. 15E is a chart that shows an exemplary pattern of the reflection coefficient phase for the activity shown in FIG. 11E, measured at 433 MHz when the antenna was placed on the right wrist.
Figure 15F:
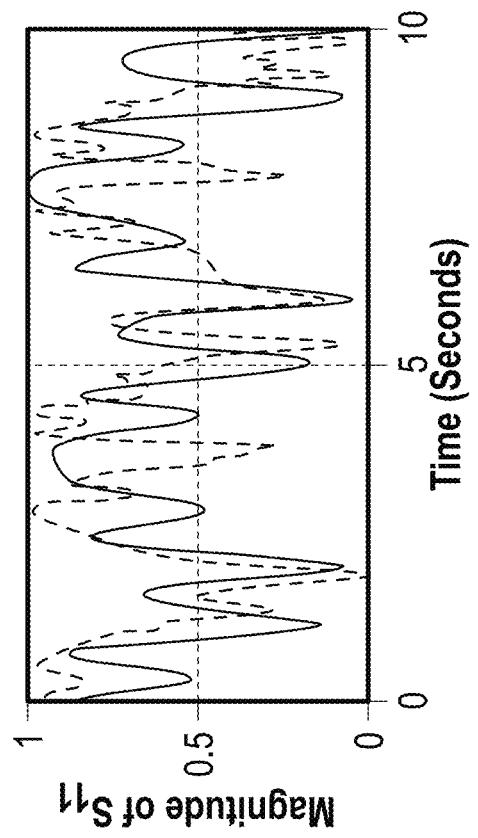
FIG. 15F is a chart that shows an exemplary pattern of the reflection coefficient phase for the activity shown in FIG. 11F, measured at 433 MHz when the antenna was placed on the right wrist.

The experimental setup and measurement results of the reflection coefficient of an on-body antenna during daily activities are described below. Two exemplary on-body locations, namely, chest and the right wrist, were selected as a comparison for the antenna placement, as shown in FIGS. 10A and 10B, respectively. FIG. 10A is an example of a monopole antenna placed on the chest of a subject for measurement of the reflected power. FIG. 10B is an example of a monopole antennas placed on the right wrist of a subject. The antennas used in the measurements were quarter-wave monopoles made of 18-gauge copper wire and placed on a finite size, "bridge-shaped" ground plane. In some embodiments, electrically small antennas can be used, including folded spherical and folded cylindrical antennas. Three sets of antennas were designed to resonate at 433, 915, and 2450 MHz, which correspond to the center frequencies of the bands commonly used for wireless body area networks. As the subject moved, the reflected power (with resulting reflection coefficients) at the two locations were recorded using a vector network analyzer under continuous-time mode with a sampling frequency of 120 Hz.

Seven volunteers, namely, four male and three female subjects, participated in the data-collection process. Each subject performed six different exemplary activities, namely, single arm swinging, both arms swinging, boxing, rowing, hopping, and sitting, as shown in FIGS. 11A-11F, respectively. Each experimental trial was measured for the S11 data for 20 seconds for two times, and the subject was asked to repeat the experiment at all three frequencies. The term "S11" is used to denote the same antenna that produces the transmitted power receives the reflected power. In total, 252 experimental data sets were collected (seven subjects*six activities*three frequencies*two trials). Other activities, number of subjects, including one subject, amount of frequencies, length of time, and number of trials can be varied as desired.

FIGS. 12A-12F are charts that show exemplary patterns for the magnitude of the reflection coefficient for the above referenced six activities measured at 433 MHz when the antenna was placed on the chest. FIGS. 13A-13F are charts that show exemplary patterns for the phase of the reflection coefficient for the above referenced six activities measured at 433 MHz when the antenna was placed on the chest. The charts in FIGS. 12A and 13A correspond to the activity shown in FIG. 11A, and so forth for the other charts of FIGS. 12B-F and FIGS. 13B-F for the activities in FIGS. 11B-11F. Similarly, FIGS. 14A-14F are charts that show exemplary patterns for the magnitude of the reflection coefficient for the above referenced six activities measured at 433 MHz when the antenna was placed on the right wrist. FIGS. 15A-15F are charts that show exemplary patterns for the phase of the reflection coefficient for the above referenced six activities measured at 433 MHz when the antenna was placed on the right wrist. The charts in FIGS. 14A and 15A correspond to the activity shown in FIG. 11A, and so forth for the other charts of FIGS. 14B-F and FIGS. 15B-F for the activities in FIGS. 11B-11F.

The magnitude and phase of the S11 data are normalized to present the variations in more details. In the above referenced figures, the solid line represents the measurement of a male subject, and the dashed line represents those of a female subject. The plots exhibit unique time-varying periodic patterns for different activities, showing the possibility of classifying activities based on the reflection coefficients from the antenna measurements. Furthermore, the phase of the antenna reflection coefficients exhibits a unique pattern similar to the magnitude. Thus, the phase can also be used for classification.

Figure 16:
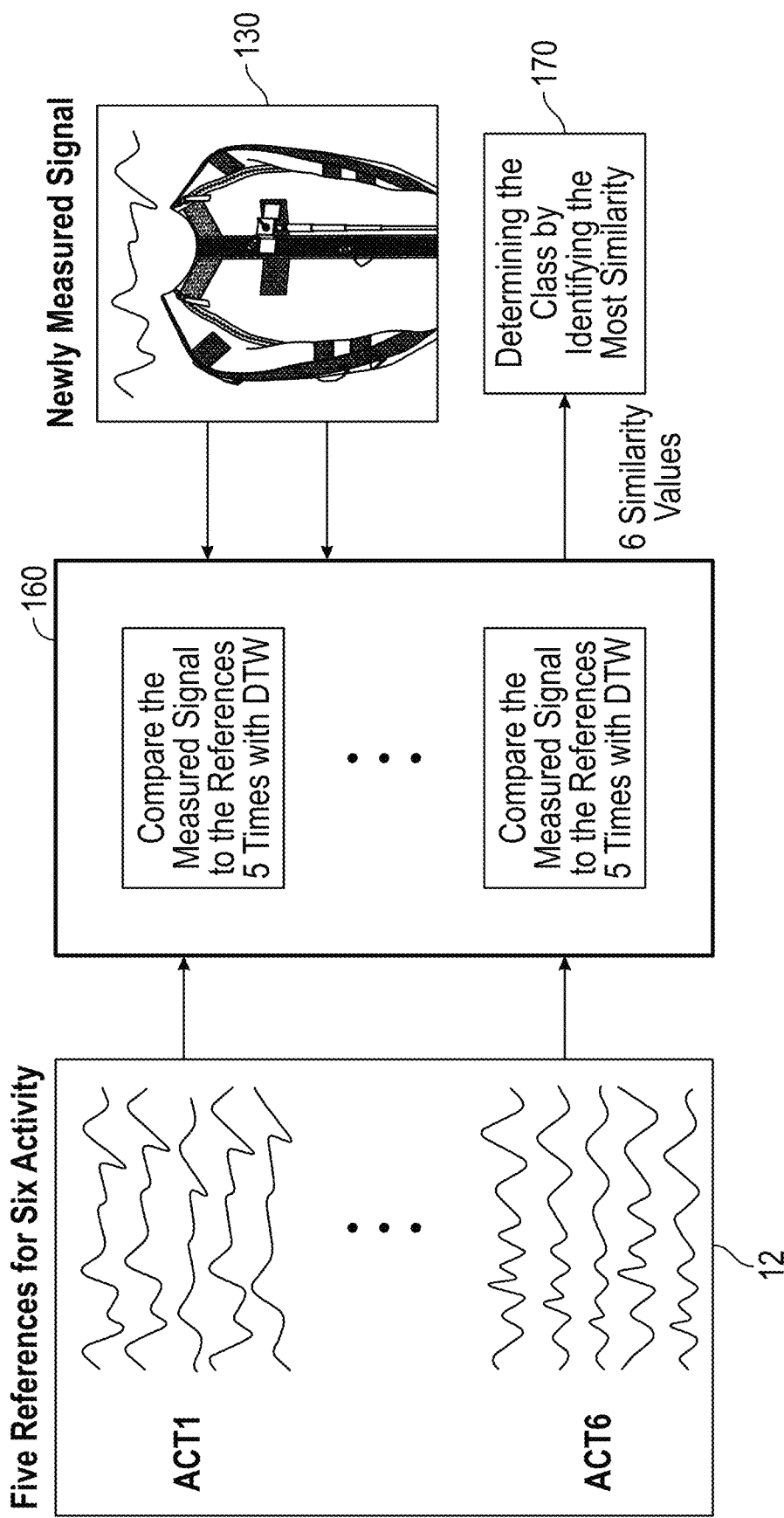
FIG. 16 is an exemplary flowchart of a process used in the experiment, referencing portions of the flow chart of FIG. 3.

FIG. 16 is an exemplary flowchart of a process used in the experiment, referencing portions of the flow chart of FIG. 3. To classify the body activities based on the above reflection coefficients of the antenna, a processing algorithm can be used such as the DTW or DLA algorithm discussed herein (or other processing algorithms). In the experiment, five random 10-second samples of data for each activity were chosen as references, although the number of samples and time duration can vary. These references can represent the calibrated patterns discussed herein to be stored in the database 12 to be used as a comparison to data for further activities that may be unclassified. When a further activity is measured in block 130, the further input data can be compared with the references in block 160, and calculate the total similarity to determine the further activity's classification in block 170.

To calculate the classification accuracy at a single frequency, ten sample data sets were extracted from each activity among the measured data sets. Therefore, the total data set becomes 420 (six activities*seven subjects*10 realization (in this example a 10-second measurement of the data)) for a given measurement frequency. The length of the extracted test data is the same as that of the references, which is 10 seconds. The input to the DTW becomes the magnitude or phase of S11. In addition, the classification accuracy was determined when both the magnitude and phase of S11 were simultaneously inputted to the DTW, because the DTW can receive multiple input vectors.

Figure 17A:
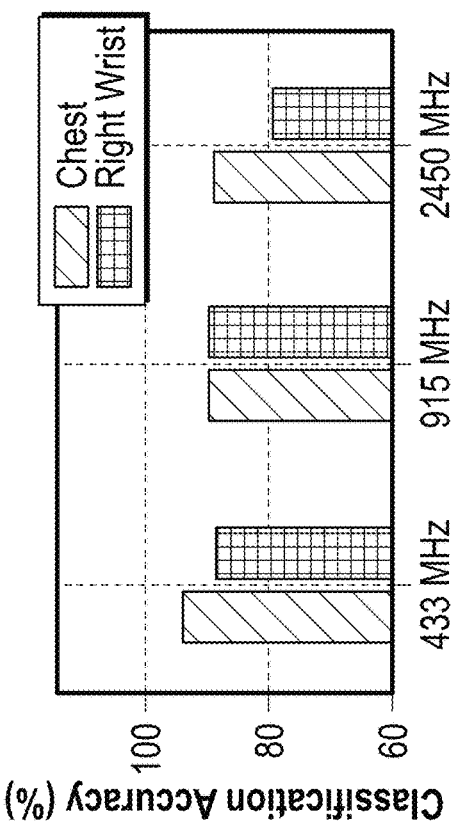
FIG. 17A is a chart showing an exemplary classification accuracy using the experimental S11 data for the three tested frequencies (433 MHz, 915 MHz, and 2450 MHz (~2.5 GHz)) in the experiment, based on the magnitude of the reflection coefficient.

FIG. 17A is a chart showing an exemplary classification accuracy using the experimental S11 data for the three tested frequencies (433 MHz, 915 MHz, and 2450 MHz (~2.45 GHz)) in the experiment, based on the magnitude of the reflection coefficient. The chart results present the chest location results on the left of the pairs of columns and the right wrist location on the right of the pairs of columns. FIG. 17A shows that the antenna on the chest and on the right wrist yielded similar classification accuracy at 433 and 915 MHz. The highest value (91.67%) was achieved for the antenna placed on the chest at 433 MHz. On the other hand, at 2.45 GHz, the accuracy from the chest location was much higher than that at the wrist, the lowest value of the data.

Figure 17B:
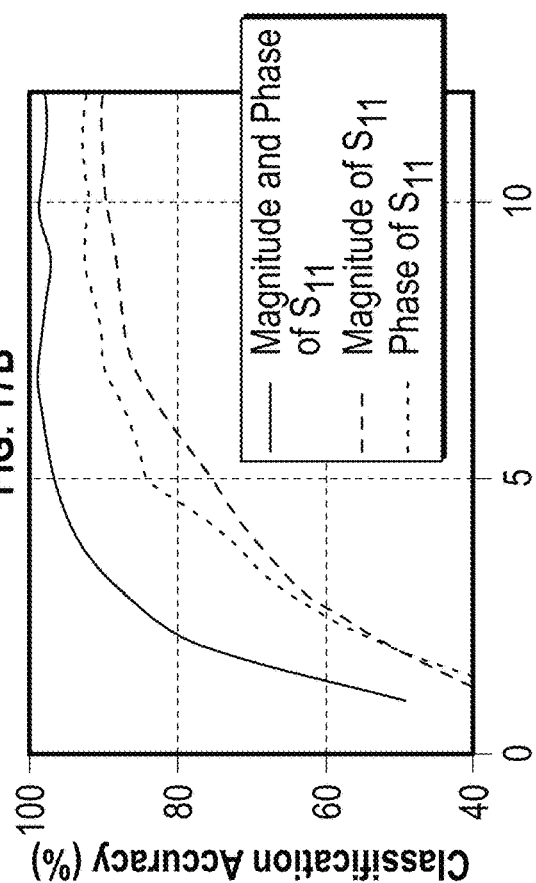
FIG. 17B is a similar chart showing the classification accuracy using the experimental S11 data, based on the phase of the reflection coefficient.

FIG. 17B is a similar chart showing the classification accuracy using the experimental S11 data, based on the phase of the reflection coefficient. FIG. 17B shows a trend similar to FIG. 17A, confirming that the phase of S11 also contained significant information regarding the activities. The highest accuracy was at the chest location with the 433 MHz and the lowest at the wrist with the 2.45 GHz.

Figure 17C:
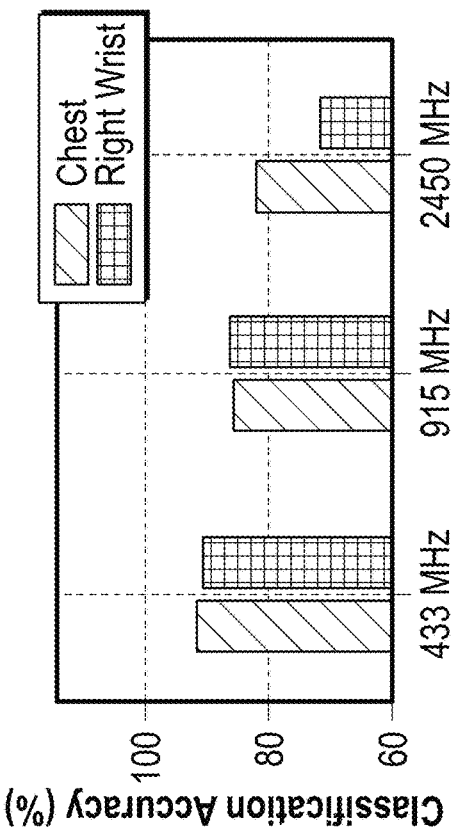
FIG. 17C is a similar chart showing the classification accuracy using the experimental S11 data, based on the combination of the magnitude and the phase of the reflection coefficient.

FIG. 17C is a similar chart showing the classification accuracy using the experimental S11 data, based on the combination of the magnitude and the phase of the reflection coefficient. FIG. 17C shows that a classification accuracy of more than 98% when the magnitude and phase were combined for the chest location and more than 96% for the wrist location. By comparing the combination of the magnitude and phase of S11 in the DTW, the similarity to the references was effectively examined and resulted in a high classification accuracy.

In addition, FIGS. 17A-17C show that the highest accuracy was achieved at 433 MHz, and the value dropped as the frequency increased. This result can be attributed to the observation that the region occupied by the near-reactive field of the antenna shrinks as the frequency increases, making the antenna reflection coefficients less sensitive to body motions outside the shrinking field.

Figure 18:
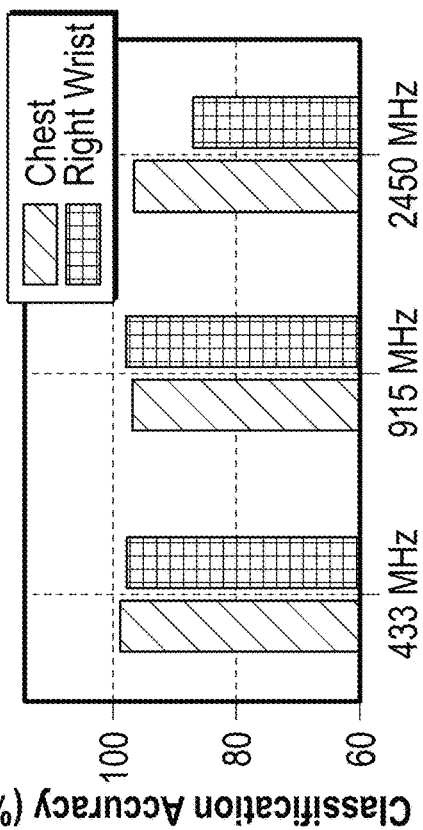
FIG. 18 is a chart showing results of the classification accuracy from the experimental data compared to the length of a time-window of the data used for comparison between patterns.

FIG. 18 is a chart showing results of the classification accuracy from the experimental data compared to the length of a time-window of the data used for comparison between patterns. The top line shows the results of combining the magnitude and phase of the reflection coefficients. The middle line shows the results of the phase of the reflection coefficient. The lower line shows the results of the magnitude of the reflection coefficient. FIG. 18 shows that the classification accuracy improved as the size of the time-window increased, that is, the length of the input data increased. The accuracy value saturated after a time-window of ten seconds for all curves, which was used for the input length in the experiment. The combination of the magnitude and phase in the top line showed a saturation level in about seven seconds. The magnitude-only lower line was the last to reach a saturation level. It is noted that the computational time also increased as the length of the input data increased.

Experiment 2

In this experiment, the above principles were applied to finger-gesture recognition. An electrically small antenna, which is a folded cylindrical helix (FCH), was selected for its advantageous characteristics of low profile and narrow resonance bandwidth. Two wrist-worn FCH antennas were designed and fabricated. The effect of a human subject on the reflection coefficient of S11 was simulated and measured, and radiated near-fields were simulated over a voxel model to understand its distribution around the arm. Next, S11 was measured with time while volunteers perform eight finger motions under two different scenarios. The dynamic time-warping (DTW) algorithm discussed above was employed to classify the measured reflection coefficient variations of the FCH for different finger activities.

Figure 19A:
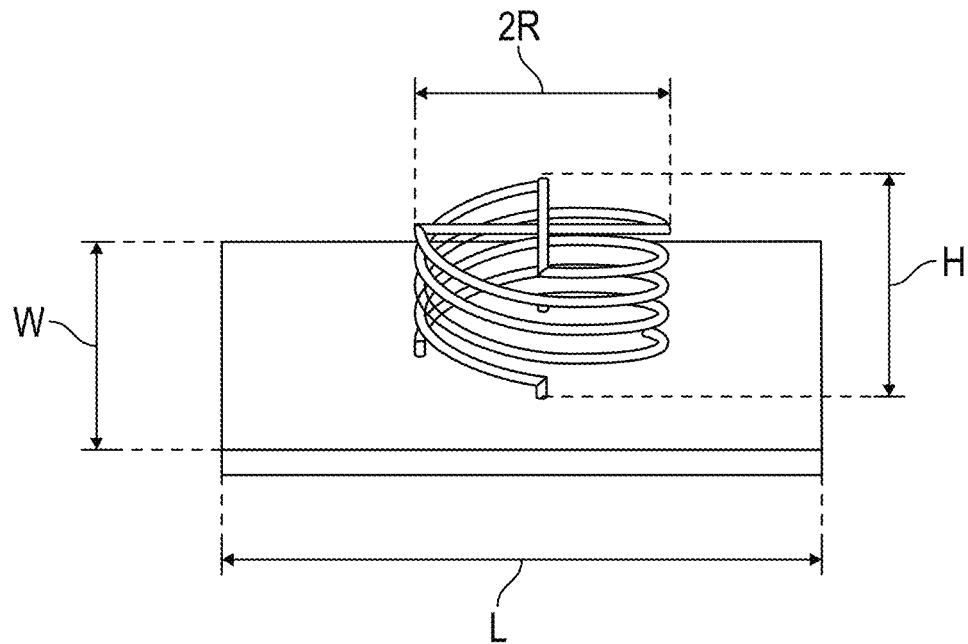
FIG. 19A is a schematic diagram of a simulation model of an exemplary antenna used for this experiment.
Figure 19B:
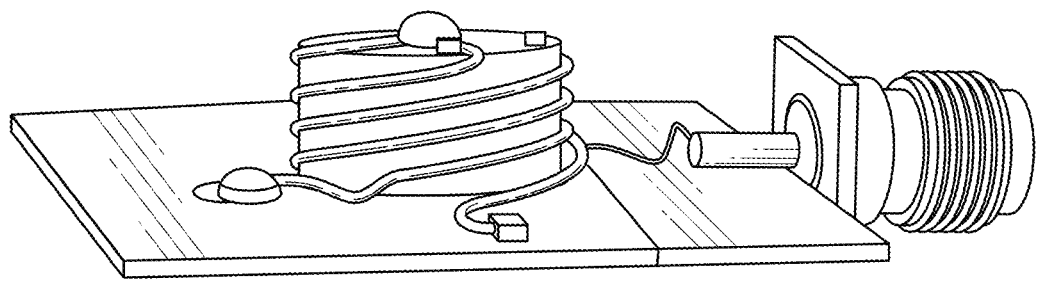
FIG. 19B is a schematic diagram of an exemplary fabricated antenna.

FIG. 19A is a schematic diagram of a simulation model of an exemplary antenna used for this experiment. FIG. 19B is a schematic diagram of an exemplary fabricated antenna. Two four-arm, one-turn FCH antennas are designed at two center frequencies around 890 MHz (type A antenna) and 2.43 GHz (type B antenna). The antenna dimensions are listed in Table I below with the heights of the FCH antennas set at less than 0.05 times the wavelength of the resonant frequencies. Both antennas were simulated using commercially available software (in this example, CST Computer Simulation Technology AG software) and fabricated using a 3D printer. In the experiment, the holding mold used to support the FCH structure was made of polylactic acid (PLA) with relative permittivity of 1.4.

| Antenna Type | A | B |
|---|---|---|
| Measured resonance frequency in open space (MHz) | 890 | 2430 |
| Height H (mm) | 14.4 | 5 |
| Helix radius R (mm) | 14.4 | 5 |
| Wire radius (mm) | 0.4 | 0.16 |
| Ground size W*L (mm*mm) | 40*40 | 25*25 |

Figure 20A:
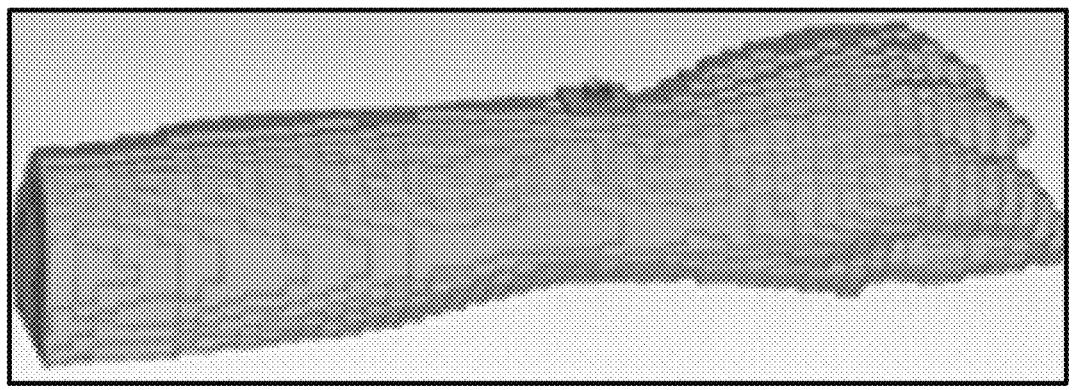
FIG. 20A is a schematic diagram of a simulation model of an exemplary arm with a simulated antenna attached to the wrist used for this experiment.

FIG. 20A is a schematic diagram of a simulation model of an exemplary arm with a simulated antenna attached to the wrist used for this experiment. The simulation model with the FCH antenna worn on the left wrist of a voxel model was created using CST software with voxel resolution of 2 mm.

Figure 20B:
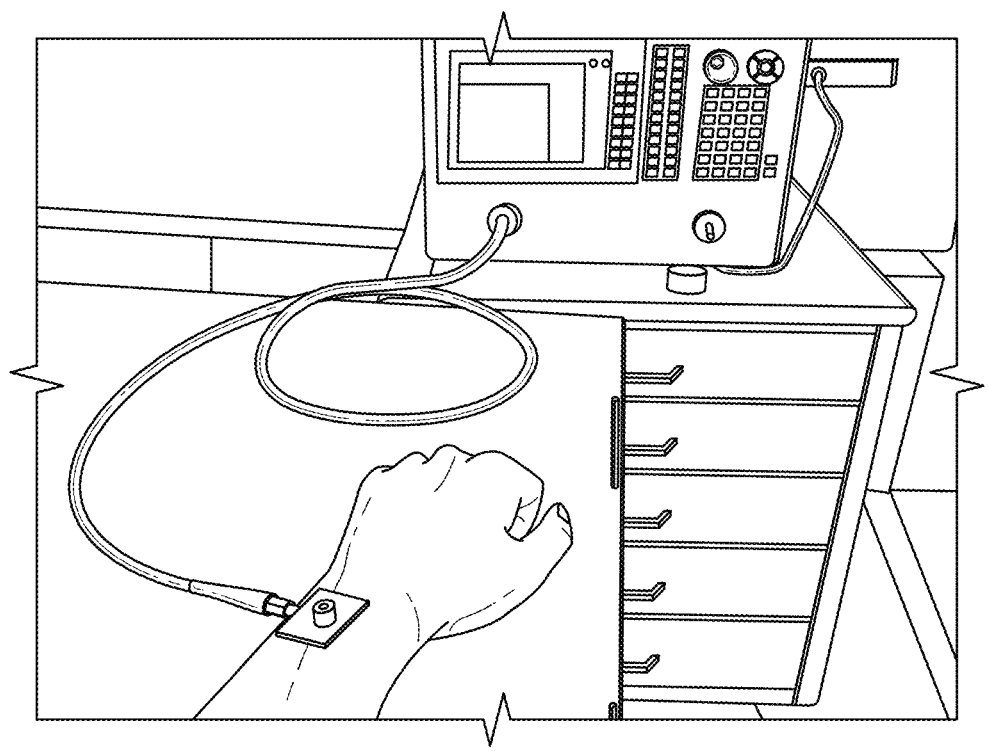
FIG. 20B is a schematic diagram of an exemplary arm of a human subject with a fabricated antenna attached to the wrist.

FIG. 20B is a schematic diagram of an exemplary arm of a human subject with a fabricated antenna attached to the wrist. The FCH antennas were simulated on a wrist of simulated arm, and the fabricated antennas were placed on the left wrist of an arm of a human subject. The reflection coefficients of the type A and B antennas were simulated and measured in a free space and on the wrist. The CST software uses the FIT algorithm, and only the left arm and hand are included in the simulation model to save simulation time.

Figure 21A:
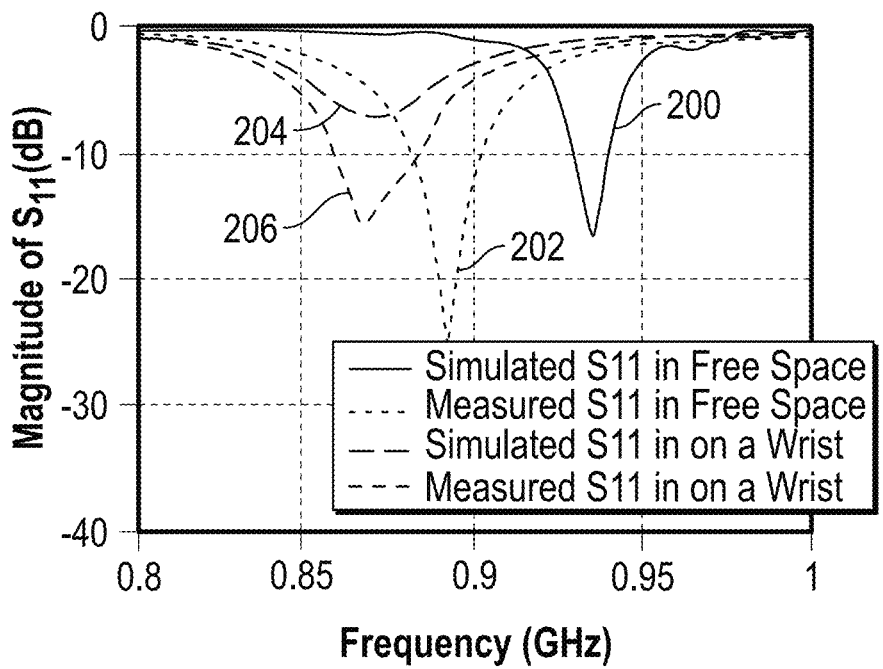
FIG. 21A is a schematic pattern chart of simulated and measured reflection coefficients of the type A antenna in free space and on the left wrist of a human subject.

FIG. 21A is a schematic pattern chart of simulated and measured reflection coefficients of the type A antenna in free space and on the left wrist of a human subject. In free space for type A antenna, the line 200 represents the simulated result, and the line 202 represents the measured result. On the wrist, the line 204 represents the simulated result, and the line 206 represents the measured result.

Figure 21B:
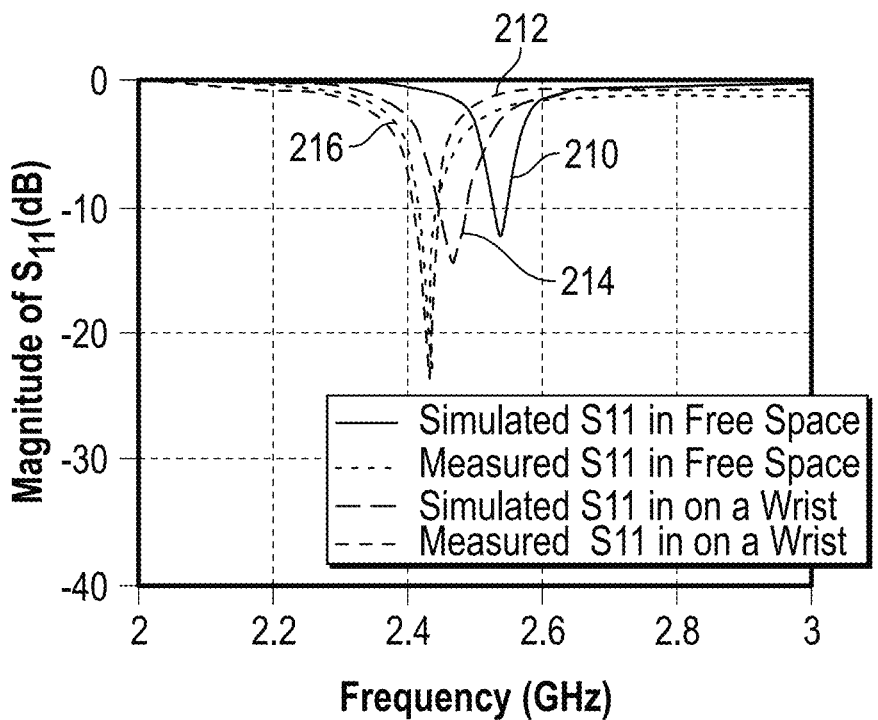
FIG. 21B is a schematic pattern chart of simulated and measured reflection coefficients of the type B antenna in free space and on the left wrist of a human subject.

FIG. 21B is a schematic pattern chart of simulated and measured reflection coefficients of the type B antenna in free space and on the left wrist of a human subject. In free space for the type B antenna, the line 210 represents the simulated result, and the line 212 represents the measured result. On the wrist, the line 214 represents the simulated result, and the line 216 represents the measured result.

The resonance frequencies of both FCH type A and B antennas shift lower when the antenna is placed on the human wrist. For both antennas, the measured resonance frequency shifts downward because of the PLA mold. The measured −10 dB fractional bandwidths are 2.2% and 1.3% for the type A and B antennas, respectively, which is a typical characteristic of electrically small antennas.

Figure 22A:
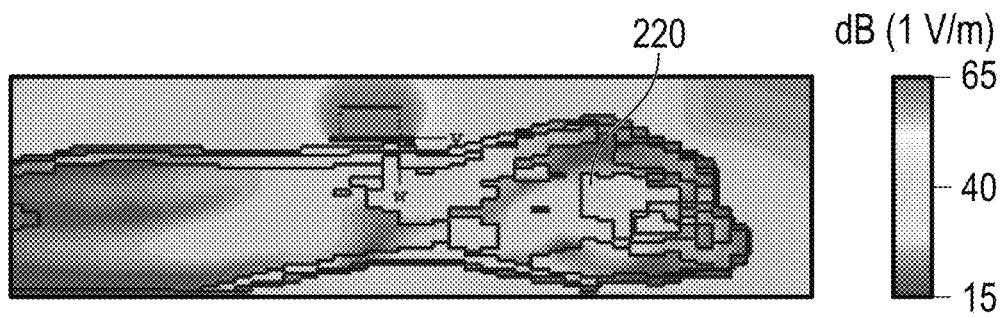
FIG. 22A is a schematic diagram of an arm, hand, and fingers with a simulated electric field intensity distribution at the resonance frequency of the type A antenna.
Figure 22B:
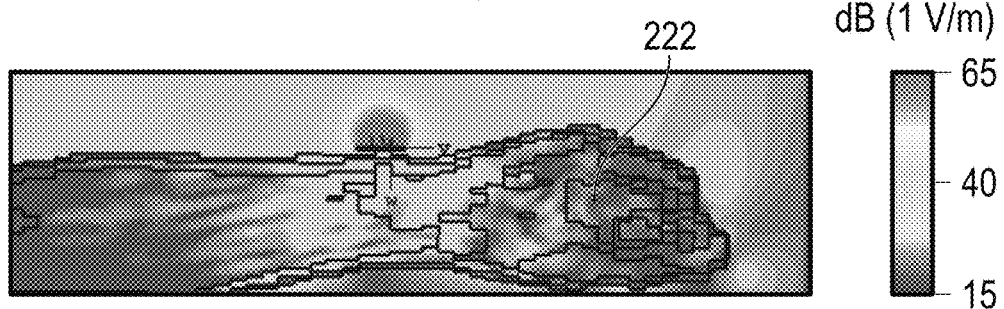
FIG. 22B is a schematic diagram of an arm, hand, and fingers with a simulated electric field intensity distribution at the resonance frequency of the type B antenna.

FIG. 22A is a schematic diagram of an arm, hand, and fingers with a simulated electric field intensity distribution at the resonance frequency of the type A antenna. FIG. 22B is a schematic diagram of an arm, hand, and fingers with a simulated electric field intensity distribution at the resonance frequency of the type B antenna. The near-field electric distributions of both wrist-worn FCH antennas at their resonance frequencies was simulated. The field intensity of the type A antenna around the fingers around zone 220 in FIG. 22A is stronger than the field intensity of the type B antenna around the fingers around zone 222 in FIG. 22B of type B. The type A antenna operates at a significantly lower frequency. Also, the electric field propagates along the surface of the hand toward the tip of the fingers in both cases as shown in the figures. As the fingers move, the near-field perturbations can cause a change in the reflection coefficient of the antenna, which can present unique patterns of variations that can be used for classification purposes.

In this experiment, finger-motion experiments used the above-designed wrist-worn FCH antennas. The antennas were mounted on the left wrist of a participant and connected to a vector network analyzer (in this example, Agilent PNL N5230C) using a coaxial cable, as shown in FIG. 20B. The antenna reflection coefficients at its resonant frequencies (870 MHz and 2460 MHz for the type A and B antennas, respectively) were recorded as the subject performed different finger motions using either the left or right hand, as described below.

Figure 23A:
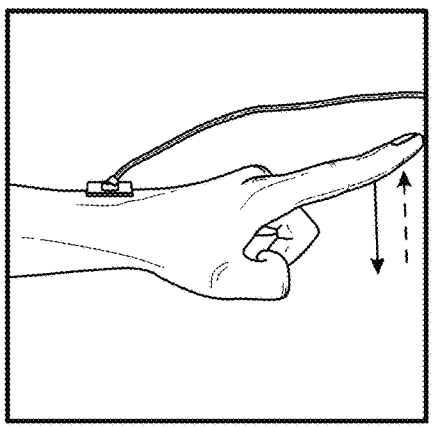
FIG. 23A is a schematic diagram of an exemplary first finger movement representing a typical click movement such as on a computer touchpad, mouse, or keyboard.
Figure 23B:
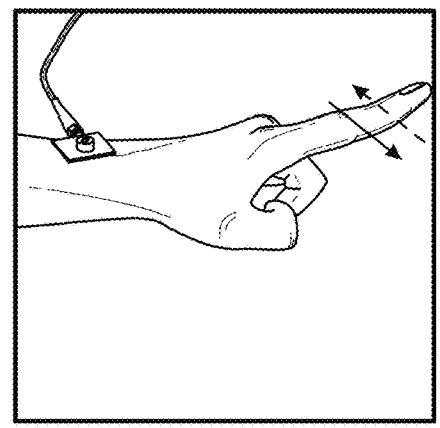
FIG. 23B is a schematic diagram of an exemplary second finger movement representing a typical swipe movement such as on a computer touchpad.
Figure 23C:
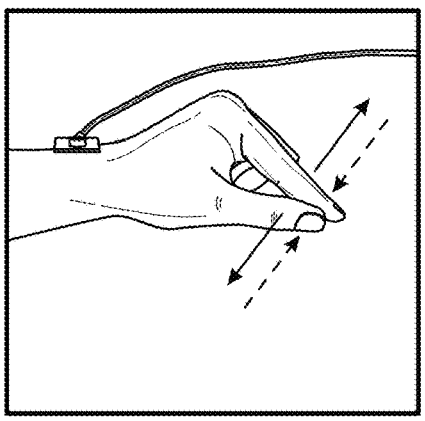
FIG. 23C is a schematic diagram of an exemplary third finger movement representing a typical zoom movement.
Figure 23D:
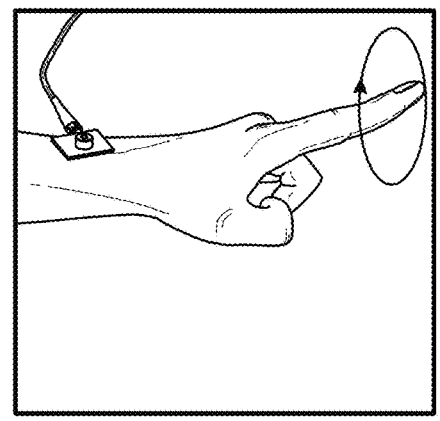
FIG. 23D is a schematic diagram of an exemplary first finger movement representing a typical circular movement.

FIG. 23A is a schematic diagram of an exemplary first finger movement representing a typical click movement such as on a computer touchpad, mouse, or keyboard. FIG. 23B is a schematic diagram of an exemplary second finger movement representing a typical swipe movement such as on a computer touchpad. FIG. 23C is a schematic diagram of an exemplary third finger movement representing a typical zoom movement. FIG. 23D is a schematic diagram of an exemplary first finger movement representing a typical circular movement. The click, swipe, zoom, and circle motions of the left-hand index finger were measured when the antenna is attached on the left wrist. These finger activities are commonly used for wireless controls and human-computer interactions. Each motion was repeated once per second and iterated for 20 seconds. Four volunteers, namely, two males and two females, participated in the experiment.

Figures 24A, 24B, 24C, 24D:
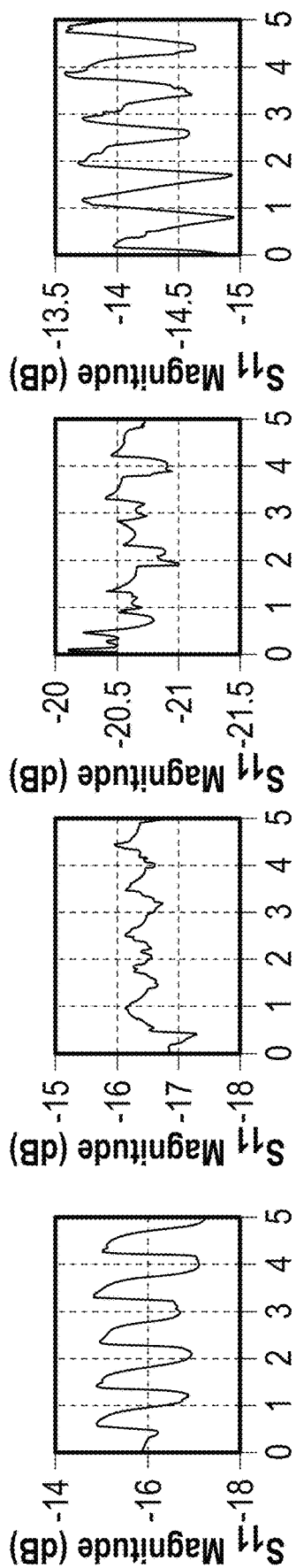
FIG. 24A is a chart that shows an exemplary pattern of the reflection coefficient magnitude for the activity shown in FIG. 23A, measured at the resonant frequency for the type A antenna on the left wrist.
FIG. 24B is a chart that shows an exemplary pattern of the reflection coefficient magnitude for the activity shown in FIG. 23B, measured at the resonant frequency for the type A antenna on the left wrist.
FIG. 24C is a chart that shows an exemplary pattern of the reflection coefficient magnitude for the activity shown in FIG. 23C, measured at the resonant frequency for the type A antenna on the left wrist.
FIG. 24D is a chart that shows an exemplary pattern of the reflection coefficient magnitude for the activity shown in FIG. 23D, measured at the resonant frequency for the type A antenna on the left wrist.

FIG. 24A is a chart that shows an exemplary pattern of the reflection coefficient magnitude for the activity shown in FIG. 23A, measured at the resonant frequency for the type A antenna on the left wrist. FIG. 24B is a chart that shows an exemplary pattern of the reflection coefficient magnitude for the activity shown in FIG. 23B, measured at the resonant frequency for the type A antenna on the left wrist. FIG. 24C is a chart that shows an exemplary pattern of the reflection coefficient magnitude for the activity shown in FIG. 23C, measured at the resonant frequency for the type A antenna on the left wrist. FIG. 24D is a chart that shows an exemplary pattern of the reflection coefficient magnitude for the activity shown in FIG. 23D, measured at the resonant frequency for the type A antenna on the left wrist.

Figures 25A, 25B, 25C, 25D:
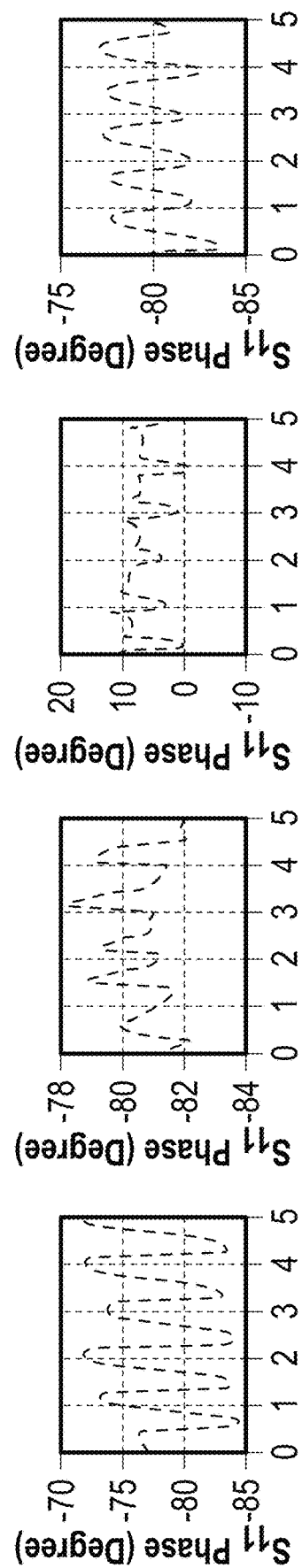
FIG. 25A is a chart that shows an exemplary pattern of the reflection coefficient phase for the activity shown in FIG. 23A, measured at the resonant frequency for the type A antenna on the left wrist.
FIG. 25B is a chart that shows an exemplary pattern of the reflection coefficient phase for the activity shown in FIG. 23B, measured at the resonant frequency for the type A antenna on the left wrist.
FIG. 25C is a chart that shows an exemplary pattern of the reflection coefficient phase for the activity shown in FIG. 23C, measured at the resonant frequency for the type A antenna on the left wrist.
FIG. 25D is a chart that shows an exemplary pattern of the reflection coefficient phase for the activity shown in FIG. 23D, measured at the resonant frequency for the type A antenna on the left wrist.

FIG. 25A is a chart that shows an exemplary pattern of the reflection coefficient phase for the activity shown in FIG. 23A, measured at the resonant frequency for the type A antenna on the left wrist. FIG. 25B is a chart that shows an exemplary pattern of the reflection coefficient phase for the activity shown in FIG. 23B, measured at the resonant frequency for the type A antenna on the left wrist. FIG. 25C is a chart that shows an exemplary pattern of the reflection coefficient phase for the activity shown in FIG. 23C, measured at the resonant frequency for the type A antenna on the left wrist. FIG. 25D is a chart that shows an exemplary pattern of the reflection coefficient phase for the activity shown in FIG. 23D, measured at the resonant frequency for the type A antenna on the left wrist.

FIG. 26A is a chart that shows an exemplary pattern of the reflection coefficient magnitude for the activity shown in FIG. 23A, measured at the resonant frequency for the type B antenna on the left wrist. FIG. 26B is a chart that shows an exemplary pattern of the reflection coefficient magnitude for the activity shown in FIG. 23B, measured at the resonant frequency for the type B antenna on the left wrist. FIG. 26C is a chart that shows an exemplary pattern of the reflection coefficient magnitude for the activity shown in FIG. 23C, measured at the resonant frequency for the type B antenna on the left wrist. FIG. 26D is a chart that shows an exemplary pattern of the reflection coefficient magnitude for the activity shown in FIG. 23D, measured at the resonant frequency for the type B antenna on the left wrist.

FIG. 27A is a chart that shows an exemplary pattern of the reflection coefficient phase for the activity shown in FIG. 23A, measured at the resonant frequency for the type B antenna on the left wrist. FIG. 27B is a chart that shows an exemplary pattern of the reflection coefficient phase for the activity shown in FIG. 23B, measured at the resonant frequency for the type B antenna on the left wrist. FIG. 27C is a chart that shows an exemplary pattern of the reflection coefficient phase for the activity shown in FIG. 23C, measured at the resonant frequency for the type B antenna on the left wrist. FIG. 27D is a chart that shows an exemplary pattern of the reflection coefficient phase for the activity shown in FIG. 23D, measured at the resonant frequency for the type B antenna on the left wrist.

As shown, each different movement creates a different pattern. Further, the magnitude variation of the type A antenna is approximately 0.5 to 1 dB greater and the phase variation is approximately 4° to 10° greater than those of the type B antenna as the subject performs the left index finger motions. This result implies that the larger near-field perturbation is caused by the lower frequency type A antenna.

Finger motions using the right hand with the antenna on the left wrist were also measured. Motions of the right hand and fingers, particularly, click, double click, zoom, and circle motions of the right-hand index finger in which movement was carried out near the antenna attached to the left wrist, as shown in FIGS. 28A-28D. These finger activities are commonly used for wireless controls and human-computer interactions. Similarly as for the left wrist movements, each motion was repeated once per second and iterated for 20 seconds. Two volunteers, namely, one male and one female, participated in the experiment.

Figure 28A:
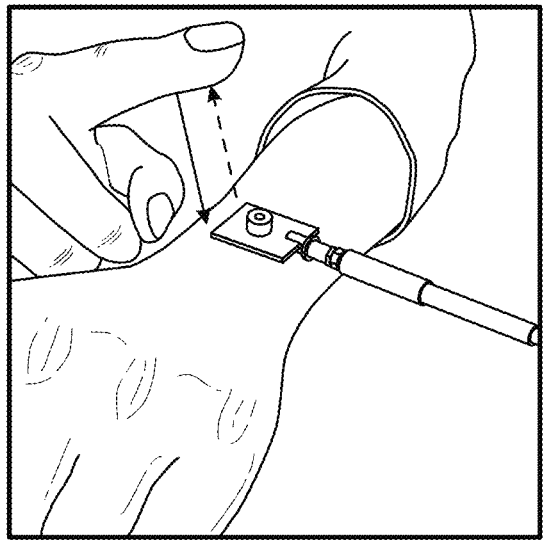
FIG. 28A is a schematic diagram of an exemplary first finger movement representing a typical click movement such as on a computer touchpad, mouse, or keyboard.
Figure 28B:
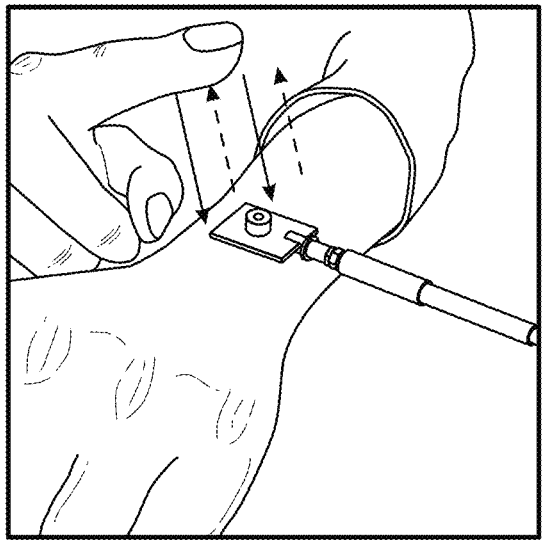
FIG. 28B is a schematic diagram of an exemplary second finger movement representing a typical doubled click movement such as on a computer touchpad.
Figure 28C:
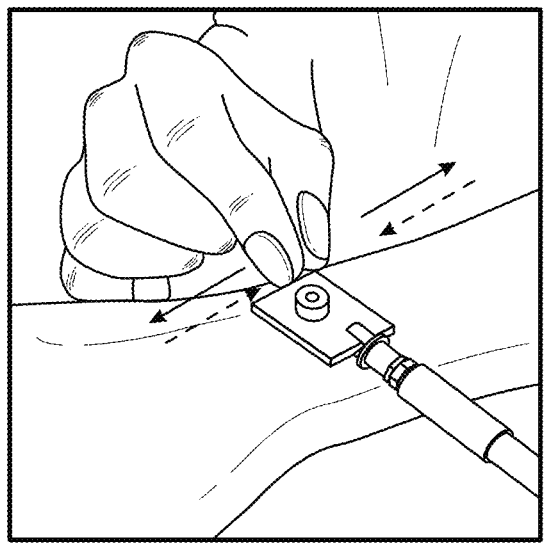
FIG. 28C is a schematic diagram of an exemplary third finger movement representing a typical zoom movement.
Figure 28D:
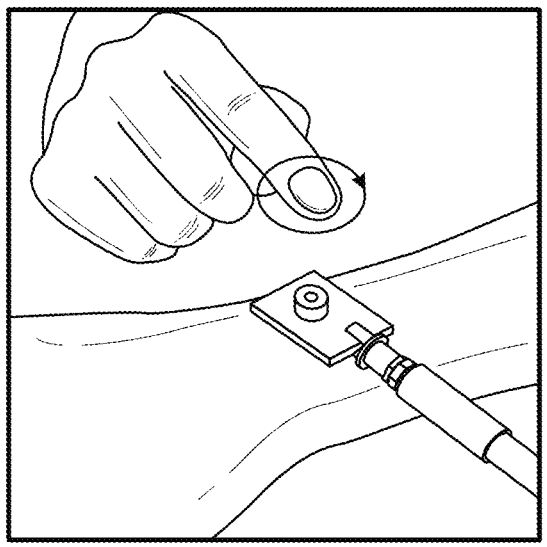
FIG. 28D is a schematic diagram of an exemplary first finger movement representing a typical circular movement.

FIG. 28A is a schematic diagram of an exemplary first finger movement representing a typical click movement such as on a computer touchpad, mouse, or keyboard. FIG. 28B is a schematic diagram of an exemplary second finger movement representing a typical doubled click movement such as on a computer touchpad. FIG. 28C is a schematic diagram of an exemplary third finger movement representing a typical zoom movement. FIG. 28D is a schematic diagram of an exemplary first finger movement representing a typical circular movement.

FIG. 29A is a chart that shows an exemplary pattern of the reflection coefficient magnitude for the activity shown in FIG. 28A, measured at the resonant frequency for the type A antenna on the left wrist. FIG. 29B is a chart that shows an exemplary pattern of the reflection coefficient magnitude for the activity shown in FIG. 28B, measured at the resonant frequency for the type A antenna on the left wrist. FIG. 29C is a chart that shows an exemplary pattern of the reflection coefficient magnitude for the activity shown in FIG. 28C, measured at the resonant frequency for the type A antenna on the left wrist. FIG. 29D is a chart that shows an exemplary pattern of the reflection coefficient magnitude for the activity shown in FIG. 28D, measured at the resonant frequency for the type A antenna on the left wrist.

FIG. 30A is a chart that shows an exemplary pattern of the reflection coefficient phase for the activity shown in FIG. 28A, measured at the resonant frequency for the type A antenna on the left wrist. FIG. 30B is a chart that shows an exemplary pattern of the reflection coefficient phase for the activity shown in FIG. 28B, measured at the resonant frequency for the type A antenna on the left wrist. FIG. 30C is a chart that shows an exemplary pattern of the reflection coefficient phase for the activity shown in FIG. 28C, measured at the resonant frequency for the type A antenna on the left wrist. FIG. 30D is a chart that shows an exemplary pattern of the reflection coefficient phase for the activity shown in FIG. 28D, measured at the resonant frequency for the type A antenna on the left wrist.

Figures 31A, 31B, 31C, 31D:
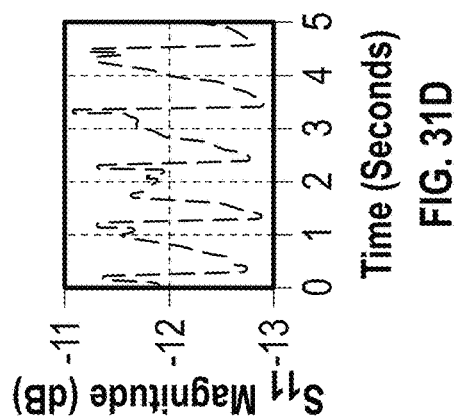
FIG. 31A is a chart that shows an exemplary pattern of the reflection coefficient magnitude for the activity shown in FIG. 28A, measured at the resonant frequency for the type B antenna on the left wrist.
FIG. 31B is a chart that shows an exemplary pattern of the reflection coefficient magnitude for the activity shown in FIG. 28B, measured at the resonant frequency for the type B antenna on the left wrist.
FIG. 31C is a chart that shows an exemplary pattern of the reflection coefficient magnitude for the activity shown in FIG. 28C, measured at the resonant frequency for the type B antenna on the left wrist.
FIG. 31D is a chart that shows an exemplary pattern of the reflection coefficient magnitude for the activity shown in FIG. 28D, measured at the resonant frequency for the type B antenna on the left wrist.

FIG. 31A is a chart that shows an exemplary pattern of the reflection coefficient magnitude for the activity shown in FIG. 28A, measured at the resonant frequency for the type B antenna on the left wrist. FIG. 31B is a chart that shows an exemplary pattern of the reflection coefficient magnitude for the activity shown in FIG. 28B, measured at the resonant frequency for the type B antenna on the left wrist. FIG. 31C is a chart that shows an exemplary pattern of the reflection coefficient magnitude for the activity shown in FIG. 28C, measured at the resonant frequency for the type B antenna on the left wrist. FIG. 31D is a chart that shows an exemplary pattern of the reflection coefficient magnitude for the activity shown in FIG. 28D, measured at the resonant frequency for the type B antenna on the left wrist.

Figures 32A, 32B, 32C, 32D:
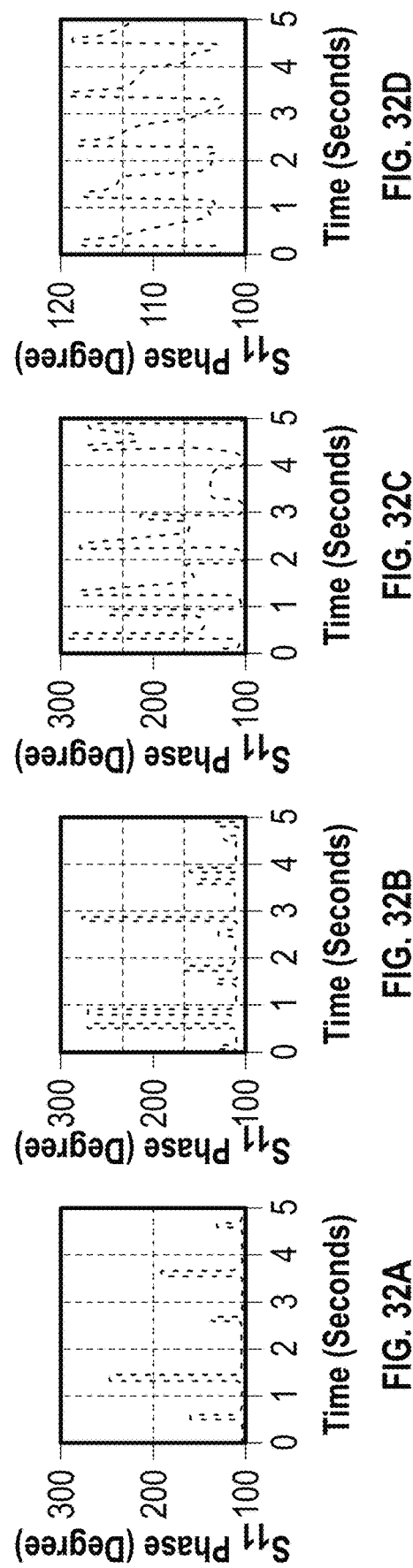
FIG. 32A is a chart that shows an exemplary pattern of the reflection coefficient phase for the activity shown in FIG. 28A, measured at the resonant frequency for the type B antenna on the left wrist.
FIG. 32B is a chart that shows an exemplary pattern of the reflection coefficient phase for the activity shown in FIG. 28B, measured at the resonant frequency for the type B antenna on the left wrist.
FIG. 32C is a chart that shows an exemplary pattern of the reflection coefficient phase for the activity shown in FIG. 28C, measured at the resonant frequency for the type B antenna on the left wrist.
FIG. 32D is a chart that shows an exemplary pattern of the reflection coefficient phase for the activity shown in FIG. 28D, measured at the resonant frequency for the type B antenna on the left wrist.

FIG. 32A is a chart that shows an exemplary pattern of the reflection coefficient phase for the activity shown in FIG. 28A, measured at the resonant frequency for the type B antenna on the left wrist. FIG. 32B is a chart that shows an exemplary pattern of the reflection coefficient phase for the activity shown in FIG. 28B, measured at the resonant frequency for the type B antenna on the left wrist. FIG. 32C is a chart that shows an exemplary pattern of the reflection coefficient phase for the activity shown in FIG. 28C, measured at the resonant frequency for the type B antenna on the left wrist. FIG. 32D is a chart that shows an exemplary pattern of the reflection coefficient phase for the activity shown in FIG. 28D, measured at the resonant frequency for the type B antenna on the left wrist.

Compared with the left-hand finger movements, the right index finger motions cause a much larger variation in both magnitude (up to 20 dB) and phase (up to 150°) for both antennas, as shown in FIGS. 29A-32D. The right index finger motion is closer to the antenna, causing larger perturbation in the near fields. Overall, both the magnitude and phase show unique patterns for different finger activities, which can be utilized for recognition purposes.

Based on the measured reflection coefficients in time domain for each gesture, the measured data can be classified to recognize its type. There are various techniques available for the classification of S11 data. Advantageously, a classification based on the previously described DTW technique was used for these movements as well. The DTW technique can calculate the optimal path between two temporal signals to calculate the similarity of them. The DTW technique generally is effective, even if the data contain distortions such as variations in speed, delay, and acceleration. In particular, the DTW technique can process multi-dimensional data, which enables the use of both the magnitude and phase of S11 as inputs to DTW for greater accuracy.

In this experiment, three signals were selected for each gesture as references not to be biased by a certain reference signal. Because the DTW technique provides the Euclidean distance between two signals, the class can be determined by identifying the reference that has the minimum distance to the measured signal. The process used Matlab.

With four participants performing four finger gestures for 20 seconds each for the first scenario with left hand movements, a total of 320 seconds (4×4×20) of data were available for testing, whereas for the second scenario with right hand movements, a total of 160 seconds (2×4×20) of data were available from two participants performing four finger gestures. From each measured 20 seconds of data, 20 samples were randomly cropped using a time window. Because each finger motion has a one-second period, the motion generally is classified using a one-second time window.

Figure 33A:
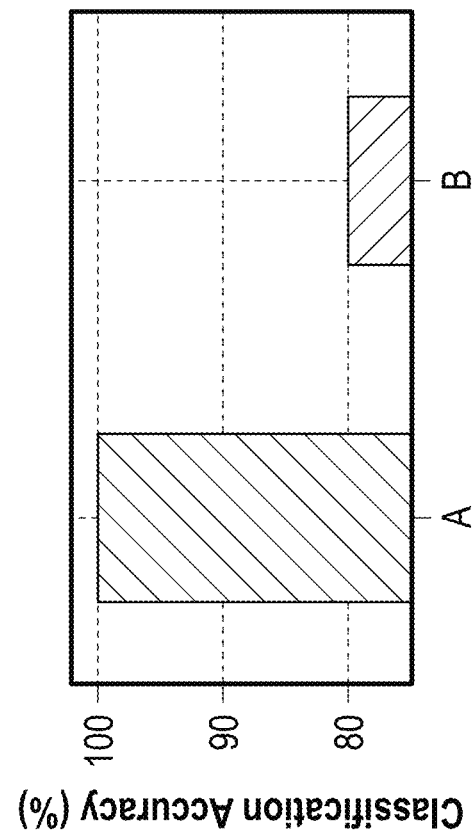
FIG. 33A is a chart showing an exemplary classification accuracy using the experimental S11 data for the two tested frequencies of the type A and B antennas in the experiment for the left hand movements.
Figure 33B:
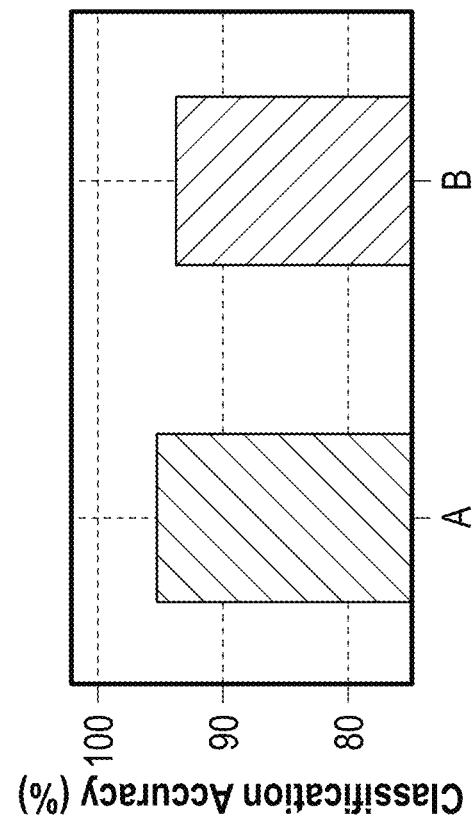
FIG. 33B is a chart showing an exemplary classification accuracy using the experimental S11 data for the two tested frequencies of the type A and B antennas in the experiment for the right hand movements.

FIG. 33A is a chart showing an exemplary classification accuracy using the experimental S11 data for the two tested frequencies of the type A and B antennas in the experiment for the left hand movements. FIG. 33B is a chart showing an exemplary classification accuracy using the experimental S11 data for the two tested frequencies of the type A and B antennas in the experiment for the right hand movements. With the implemented classifier using DTW for a combination of magnitude and phase of the reflection coefficients, the results are shown in FIGS. 33A and 33B for both scenarios described above for left hand and right hand movements with the left wrist mounted antennas types A and B. In all cases of the test data, both types A and B antennas can provide classification accuracies above 80%. For comparison, the type A antenna shows a higher classification accuracy for both scenarios, indicating a higher accuracy using the lower frequency antenna. In addition, the second scenario with right hand movement shows better results than the first scenario with left hand movement, especially using the type A antenna. These results in the second scenario are likely due to the right hand movements being conducted in close proximity to the antenna mounted on the left wrist, as shown in FIGS. 28A-28D.

Figure 34A:
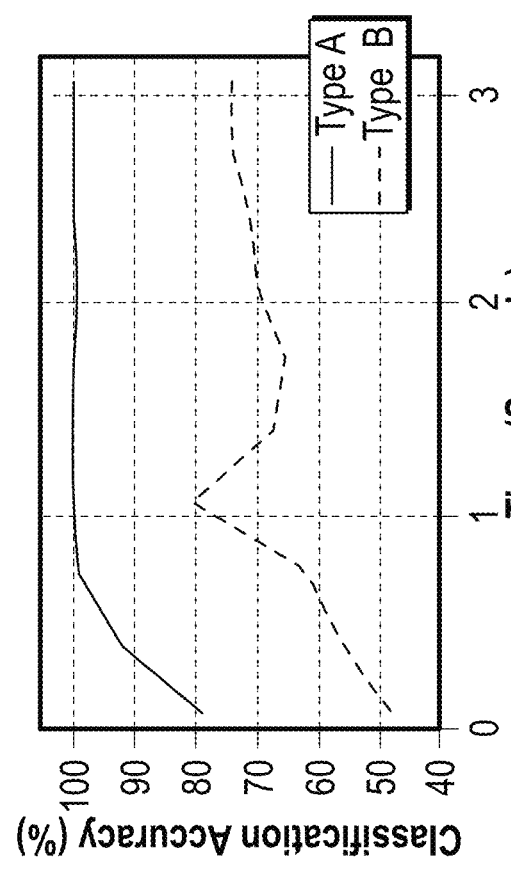
FIG. 34A is a chart showing results of the classification accuracy from the experimental data compared to the length of a time-window of the data used for comparison between patterns for the left hand movements with the type A and B antennas coupled to the left wrist.
Figure 34B:
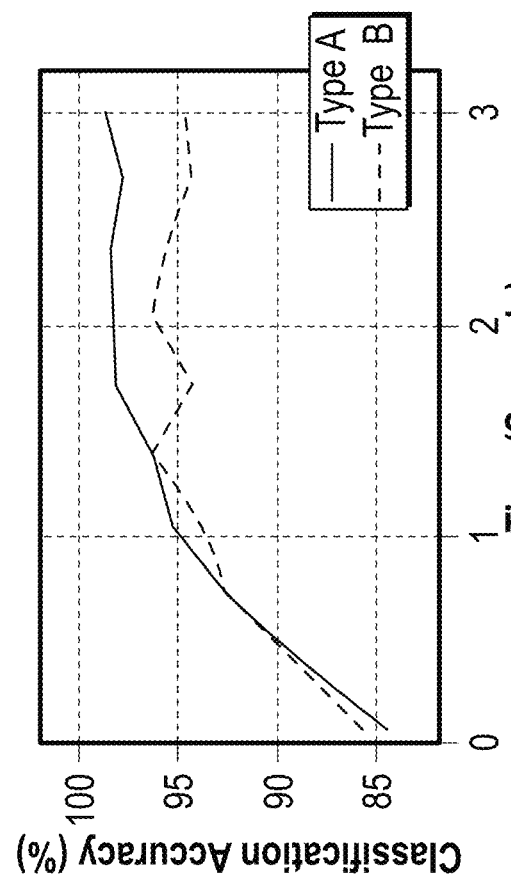
FIG. 34B is a chart showing results of the classification accuracy from the experimental data compared to the length of a time-window of the data used for comparison between patterns for the right hand movements with the type A and B antennas coupled to the left wrist.

FIG. 34A is a chart showing results of the classification accuracy from the experimental data compared to the length of a time-window of the data used for comparison between patterns for the left hand movements with the type A and B antennas coupled to the left wrist. FIG. 34B is a chart showing results of the classification accuracy from the experimental data compared to the length of a time-window of the data used for comparison between patterns for the right hand movements with the type A and B antennas coupled to the left wrist. To investigate the necessary time-window size to obtain acceptable classification accuracy, the window was varied from 0.1 to 3 second. In general, a larger time window increases the classification accuracy, because the signatures would be repeatedly included, whereas longer time is needed to acquire the data.

In FIG. 34A for the left hand movements, the overall classification accuracy of the type A antenna is higher than that of the type B antenna. The accuracy saturates to approximately 97% and 95%, respectively, when the window size is more than 1.5 seconds. In FIG. 34B for the right hand movements, the type A antenna shows the best performance with approximately 100% accuracy.

The results show that finger motions can be recognized using the variation of wrist-worn antenna reflection coefficients. Eight different finger motions from both left and right index fingers were monitored by recording the time-varying reflection coefficient of two FCH antennas. The DTW classification results indicate that the performance of the type A antenna is better than that of the type B antenna, and the maximum classification accuracy can reach up to 97% for the left index finger motion and 100% for right index finger motion with the left wrist mounted antenna.

Other and further embodiments utilizing one or more aspects of the inventions described above can be devised without departing from the disclosed invention as defined in the claims. For example, wearable directional antennas with maximum radiation direction pointing to the finger could be used for increased sensitivity to finger motions and less sensitivity to the environment. Other planar type antennas that can be implemented inside wrist-worn devices for the gesture detection applications discussed herein. Furthermore, RF circuits can be designed to be embedded in a wearable device to monitor the variations in S11 data, different frequencies can be used, a "computer system" could be integrated into the antenna to provide local output, such as a smart phone application, along with other variations can occur in keeping within the scope of the claims, and other variations.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

REFERENCES

[1] T. B. Moeslund, A. Hilton, and V. Krüger, "A survey of advances in vision-based human motion capture and analysis," Computer Vision and Image Understanding, vol. 104, no. 2, pp. 90-126, 2006.

[2] J. Aggarwal and Q. Cai, "Human motion analysis: A review," Computer Vision and Image Understanding, vol. 73, pp. 428-440, 1999.

[3] Google soli wearable radar: https://atap.google.com/soli/

[4] Y. Kim and B. Toomajian, "Hand gesture recognition using micro-Doppler signatures with convolutional neural network," IEEE Access, issue 99, pp. 1-5, 2016.

[5] C. Xu, P. H. Pathak, and P. Mohapatra, "Finger-writing with smartwatch: A case for finger and hand gesture recognition using smartwatch," Proc. 16th Int. Workshop Mobile Computing Systems Applications, pp. 9-14, 2015.

[6] J. Wu, L. Sun, and R. Jafari, "A wearable system for recognizing American sign language in real-time using IMU and surface EMG sensors," IEEE Journal Biomedical Health Informatics, vol. 20, pp. 1281-1290, 2016.

[7] S. M. Mane, R. A. Kambli, F. S. Kazi, and N. M. Singh, "Hand motion recognition from single channel surface EMG using wavelet & artificial neural network," Procedia Computer Science, vol. 49, pp. 58-65, 2015.

[8] A. Serra, P. Nepa, G. Manara, G. Corsini, and J. L. Volakis, "A single on-body antenna as a sensor for cardiopulmonary monitoring," IEEE Antennas and Wireless Propagat. Letters, vol. 9, pp. 930-933, 2010.

[10] S. Best, "A comparison of the cylindrical folded helix Q to the Gustafsson limit," in Proc. EuCAP, Berlin, Germany, pp. 2554-2557, March 2009.

[11] H. Sakoe and S. Chiba, "Dynamic programming algorithm optimization for spoken word recognition," IEEE Trans. Acoustics, Speech, Signal Process, vol. 26, pp. 43-49, February 1978.

What is claimed is:

1. A method of electronically classifying a body activity of a body, comprising:
electronically measuring changing reflected power with an antenna configured to wirelessly radiate signals around a human body, the changing reflected power due to perturbations in a near-field caused by the body activity;
processing the measured reflected power to create data to establish a pattern for the body activity;
electronically comparing the pattern with known patterns for known body activities; and
electronically classifying the body activity based on a correlation of the pattern with the known patterns.

2. The method of claim 1, further comprising calibrating the antenna with a body activity, comprising:
electronically measuring reflected power with the antenna while the body conducts the body activity;
electronically processing the reflected power measurements during the body activity to create data to establish a pattern to correlate with the body activity based on changes in reflected power occurring during the body activity;
storing the data for the pattern that is correlated with the body activity; and
repeating the process for other body activities to create a data set of known body activity patterns.

3. The method of claim 2, wherein the body activities are preselected for calibrating the antenna.

4. The method of claim 2, further moving the antenna to another location on the body and recalibrating the antenna with the steps of claim 2.

5. The method of claim 1, wherein processing the measured reflected power to create data to establish the pattern for the body activity comprises processing the measured reflected power to show a change in a reflection coefficient for the body activity.

6. The method of claim 1, wherein comparing the pattern with the known patterns comprises processing the data with time-varying algorithms.

7. The method of claim 1, wherein comparing the pattern with the known patterns comprises comparing a magnitude, phase, or a combination of magnitude and phase of the measured reflected power.

8. A system for classifying body activities of a body, comprising:
an antenna configured to wirelessly radiate signals around a human body to create a near-field sensitive to reflected power and configured to receive data on changing body reflected power from the body caused by perturbations in the near-field during body activities, the antenna further configured to be located on the body and send data on the body reflected power as measurements;
another receiver electromagnetically coupled with the antenna to receive signals from the antenna on the measurements;
a processor configured to determine changes in the measurements and transform the measurements into data of reflection coefficients correlated with the body activities; and
a memory to store data of the measurements, reflection coefficients, or a combination thereof.

9. The system of claim 8, further comprising a database containing the data in the memory, and the processor configured to compare the data on the body activities with corresponding measurements of further body activities for classification of the further body activities.

10. The method of claim 1, wherein the reflected power comprises a wave form.

11. The method of claim 10, wherein the reflected power can be transmitted wirelessly in the wave form.

12. The system of claim 8, wherein the reflected power comprises a wave form.

13. The method of claim 12, wherein the signals from the antenna to the another receiver are transmitted wirelessly in the wave form.

14. The method of claim 1, wherein the body activities are conducted within the near-field and remote to the antenna.

15. The system of claim 8, wherein the body activities are conducted within the near-field and remote to the antenna.

* * * * *